(12) United States Patent
Daio et al.

(10) Patent No.: US 12,396,902 B2
(45) Date of Patent: Aug. 26, 2025

(54) ABSORBENT ARTICLE INCLUDING ABSORBENT BODY AND FRONT EXTERIOR BODY DISPOSED IN FRONT WAISTLINE REGION ON NON-SKIN SURFACE SIDE OF ABSORBENT BODY

(71) Applicant: UNICHARM CORPORATION, Ehime (JP)

(72) Inventors: Mamoru Daio, Kagawa (JP); Etsuko Kudo, Kagawa (JP); Yuki Hashino, Kagawa (JP)

(73) Assignee: UNICHARM CORPORATION, Ehime (JP)

(*) Notice: Subject to any disclaimer, the term of this patent is extended or adjusted under 35 U.S.C. 154(b) by 1403 days.

(21) Appl. No.: 16/906,858

(22) Filed: Jun. 19, 2020

(65) Prior Publication Data

US 2020/0315864 A1 Oct. 8, 2020

Related U.S. Application Data

(63) Continuation of application No. PCT/JP2018/046962, filed on Dec. 20, 2018.

(30) Foreign Application Priority Data

Dec. 28, 2017 (JP) ................................ 2017-253845
Dec. 28, 2017 (JP) ................................ 2017-253852
Dec. 28, 2017 (JP) ................................ 2017-253860

(51) Int. Cl.
*A61F 13/49* (2006.01)
*A61F 13/494* (2006.01)
*A61F 13/53* (2006.01)

(52) U.S. Cl.
CPC .. *A61F 13/49061* (2013.01); *A61F 13/49007* (2013.01); *A61F 13/49446* (2013.01); *A61F 13/53* (2013.01); *A61F 2013/49098* (2013.01)

(58) Field of Classification Search
None
See application file for complete search history.

(56) References Cited

U.S. PATENT DOCUMENTS

2001/0016720 A1\* 8/2001 Otsubo ................. A61F 13/496
604/401
2004/0122412 A1\* 6/2004 Morman ............. A61F 13/5622
604/385.101

FOREIGN PATENT DOCUMENTS

CN 1224606 A 8/1999
CN 103717188 A 4/2014
(Continued)

OTHER PUBLICATIONS

Hearing Notice issued in corresponding Indian Patent Application No. 202027023492, dated May 4, 2024 (10 pages).
(Continued)

*Primary Examiner* — Michele Kidwell
(74) *Attorney, Agent, or Firm* — Osha Bergman Watanabe & Burton LLP

(57) ABSTRACT

An absorbent article includes: front waistline region; rear waistline region; crotch region disposed between front waistline region and rear waistline region; absorbent body that straddles crotch region, front waistline region, and rear waistline region; front exterior body disposed in front waistline region on non-skin surface side of absorbent body. Absorbent body includes absorbent core and front end part extending toward front side from absorbent core, a liquid-impermeable sheet and a liquid-permeable body sheet overlapping liquid-impermeable sheet in thickness direction are disposed at the front end part of absorbent body. Absorbent article includes: sheet non-bonding region where liquid-impermeable sheet and body sheet are not bonded; and body non-bonding region where absorbent body and front exterior body are not bonded. Front end part includes duplicating (Continued)

region where sheet non-bonding region and body non-bonding region overlap to each other.

10 Claims, 9 Drawing Sheets

(56) References Cited

FOREIGN PATENT DOCUMENTS

| EP | 0933073 A2 | 8/1999 |
|---|---|---|
| EP | 0933073 A3 | 8/1999 |
| JP | H11206809 A | 8/1999 |
| JP | 2005517461 A | 6/2005 |
| JP | 2008113684 A | 5/2008 |
| JP | 2014108294 A | 6/2014 |
| JP | 2016034341 A | 3/2016 |
| WO | 2013125553 A1 | 8/2013 |
| WO | 2015001915 A1 | 1/2015 |
| WO | 2016/158746 A1 | 10/2016 |
| WO | 2017159294 A1 | 9/2017 |

OTHER PUBLICATIONS

International Search Report issued in corresponding International Application No. PCT/JP2018/046962, mailed Mar. 26, 2019, with translation (4 pages).

Office Action issued in corresponding European Patent Application No. 18896688.1, dated Jan. 3, 2023 (4 pages).

Examination Report issued in corresponding Indian Patent Application No. 202027023492, mailed Jun. 22, 2022 (5 pages).

Office Action issued in corresponding Chinese Patent Application No. 201880083133.6, mailed on Jun. 30, 2021 (15 pages).

Extended European Search Report issued in corresponding European Patent Application No. 18896688.1, mailed on Jul. 30, 2021 (9 pages).

Notice of Reasons for Refusal issued in corresponding Japanese Patent Application No. 2017-253860 mailed Feb. 1, 2022 (13 pages).

Notice of Reasons for Refusal issued in corresponding Japanese Patent Application No. 2017-253845 mailed Feb. 1, 2022 (7 pages).

* cited by examiner

ABSORBENT ARTICLE INCLUDING ABSORBENT BODY AND FRONT EXTERIOR BODY DISPOSED IN FRONT WAISTLINE REGION ON NON-SKIN SURFACE SIDE OF ABSORBENT BODY

CROSS-REFERENCE TO RELATED APPLICATIONS

The present application claims priority to Japanese Patent Application Nos. 2017-253845 filed on Dec. 28, 2017, 2017-253852 filed on Dec. 28, 2017, and 2017-253860 filed on Dec. 28, 2017, which are incorporated herein by reference and are regarded as a part of the description of this specification.

BACKGROUND

Technical Field

The present invention relates to an absorbent article such as a disposable diaper.

Description of the Related Art

The absorbent article described in Patent Literature 1 has an absorbent body and an exterior body arranged on a non-skin surface side of the absorbent body. The absorbent body is fixed to the skin surface side of the exterior body (See FIG. 3 of Patent Literature 1). The absorbent body has an absorbent core and a front end part extending toward the front side relative to the absorbent core. The front end part has a liquid-impermeable sheet and a body sheet overlapping the liquid-impermeable sheet in the thickness direction.

PATENT LITERATURE

[Patent Literature 1] JP 2016-34341 A

The absorbent article thus configured generally has the highest rigidity in the region where the absorbent core is arranged. The rigidity of the front end part of the absorbent body is the second highest after the rigidity of the region where the absorbent core is arranged, and the rigidity of the region where only the exterior body is arranged is lower than the rigidity of the front end part of the absorbent body. When the wearer moves his leg back and forth, a force moving in the front-rear direction is applied to the absorbent core, and the front end part of the absorbent body moves forward via the absorbent core, so that the exterior body having relatively low rigidity easy to deform. At this time, the exterior body deforms by a force applied from the absorbent core and the absorbent body that are located on the skin surface side toward the exterior body located on the non-skin surface side, and hence the exterior body is easy to float away from the wearer. There was a risk that the position of the exterior body arranged in the front waistline region was shifted by floating away from the wearer.

Therefore, an absorbent article is required to suppress the position shift of the exterior body in the front waistline region by moving the leg of the wearer.

SUMMARY

An absorbent article according to one or more embodiments includes a front-rear direction, a width direction orthogonal to the front-rear direction, a front waistline region, a rear waistline region, a crotch region arranged between the front waistline region and the rear waistline region, an absorbent body, and a front exterior body arranged in the front waistline region on a non-skin surface side of the absorbent body. The absorbent body has an absorbent core and a front end part extending to a front side relative to the absorbent core. At least a liquid-impermeable sheet and a liquid-permeable body sheet overlapping the liquid-impermeable sheet in a thickness direction are arranged at the front end part of the absorbent body. The absorbent article is provided with a sheet non-bonding region where the liquid-impermeable sheet and the body sheet are not bonded, and a body non-bonding region where the absorbent body and the front exterior body are not bonded. The front end part of the absorbent body is provided with a duplicating region where the sheet non-bonding region and the body non-bonding region overlap.

An absorbent article according to one or more embodiments includes a front-rear direction, a width direction orthogonal to the front-rear direction, a front waistline region, a rear waistline region, a crotch region arranged between the front waistline region and the rear waistline region, an absorbent body, and a front exterior body arranged in the front waistline region on a non-skin surface side of the absorbent body. The absorbent body has an absorbent core and a front end part extending to a front side relative to the absorbent core. The front end part of the absorbent body is provided with an overlapping region where a first sheet material and a second sheet material overlap in a thickness direction. A front end edge of the overlapping region is provided with a sheet non-bonding region where the first sheet material is not bonded to the second sheet material.

An absorbent article according to one or more embodiments includes a front-rear direction, a width direction orthogonal to the front-rear direction, a front waistline region, a rear waistline region, a crotch region arranged between the front waistline region and the rear waistline region, an absorbent body, a front exterior body arranged in the front waistline region to overlap the absorbent body in a thickness direction, a rear exterior body arranged in the front waistline region to overlap the absorbent body in a thickness direction, and a side bonded portion which bonds an outside part of the front exterior body in the width direction and an outside part of the rear exterior body in the width direction. The front exterior body has a plurality of exterior sheets. A front side relative to a front end edge of the absorbent body is provided with an exterior non-bonding region where at least two of the exterior sheets are not bonded together.

DETAILED DESCRIPTION (1) Outline of Embodiments

Figure 1:
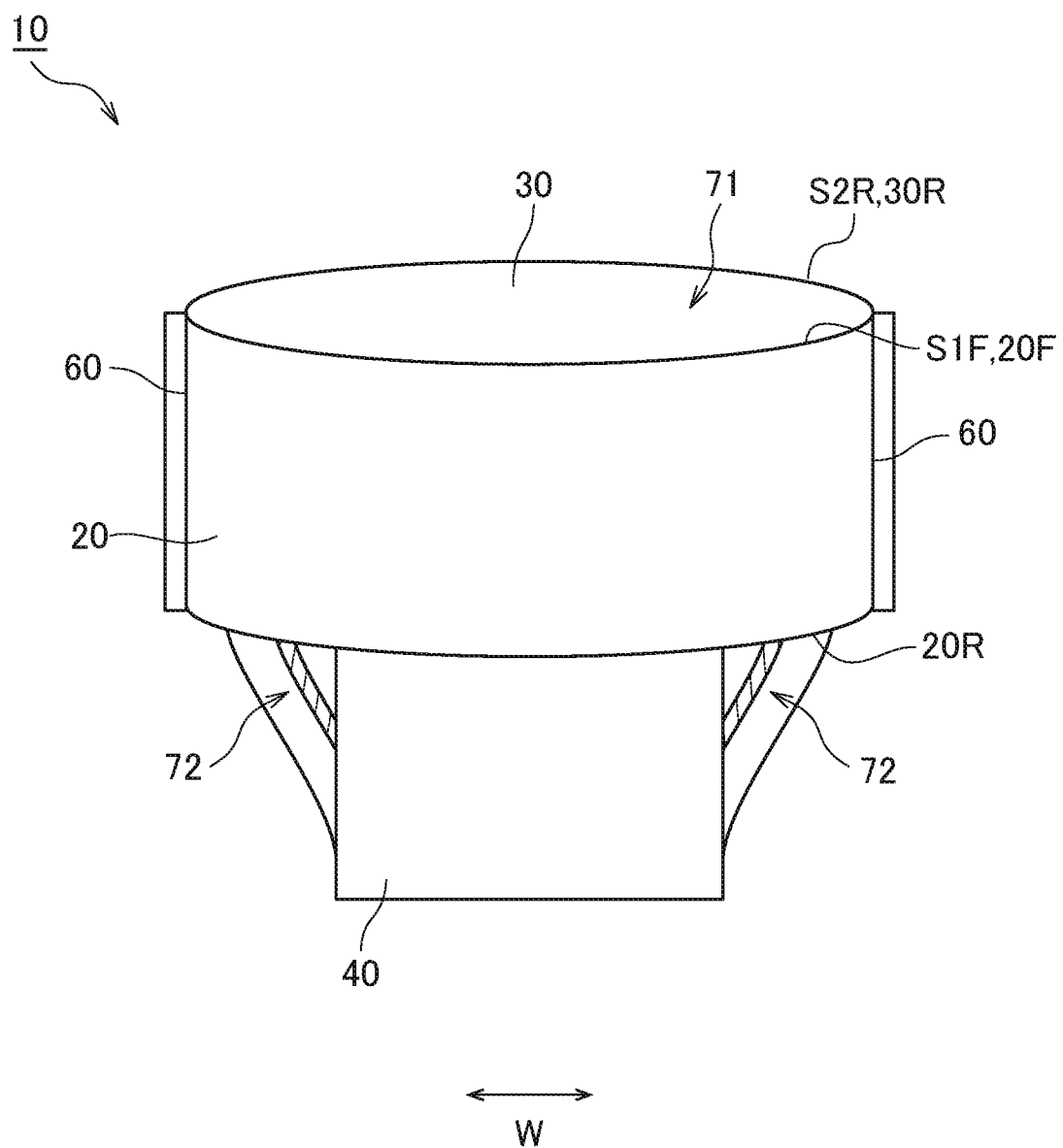
FIG. 1 is a front view of an absorbent article according to one or more embodiments.

According to the present specification and the accompanying drawings, at least the following matters are disclosed.

An absorbent article according to one or more embodiments includes a front-rear direction, a width direction orthogonal to the front-rear direction, a front waistline region, a rear waistline region, a crotch region arranged between the front waistline region and the rear waistline region, an absorbent body, and a front exterior body arranged in the front waistline region on a non-skin surface side of the absorbent body. The absorbent body has an absorbent core and a front end part extending to a front side relative to the absorbent core. At least a liquid-impermeable sheet and a liquid-permeable body sheet overlapping the liquid-impermeable sheet in a thickness direction are arranged at the front end part of the absorbent body. The absorbent article is provided with a sheet non-bonding region where the liquid-impermeable sheet and the body sheet are not bonded, and a body non-bonding region where the absorbent body and the front exterior body are not bonded. The front end part of the absorbent body is provided with a duplicating region where the sheet non-bonding region and the body non-bonding region overlap.

A duplicating region is provided at the front end part of the absorbent body, and hence the duplicating region is easy to deform when a force moving forward is applied from the absorbent core. The deformation of the front end part of the absorbent body makes it difficult for the absorbent body to push up the front exterior body. It is possible to suppress deformation such that the front exterior body floats, to suppress position shift of the front exterior body, and to continuously cover the abdomen of the wearer.

According to one or more embodiments, at least a part of the duplicating region is arranged to overlap the absorbent core in the front-rear direction.

The region arranged to overlap the absorbent core in the front-rear direction is easy to be subjected to a force directed from the absorbent core to the front side. By providing the duplicating region in at least a part of the region, deformation due to the absorbent core is absorbed by the front end part of the absorbent body, and position shift of the exterior body in the front waistline region and the rear waistline region can be suppressed.

According to one or more embodiments, the absorbent body has a central region which is a region obtained by dividing the total length of the absorbent core in the width direction into three equal parts and is located at the center of the absorbent core in the width direction, and the duplicating region is arranged to overlap the central region in the front-rear direction.

When the wearer moves his leg in the front-rear direction with the absorbent core sandwiched between the legs of the wearer, the force is easy to concentrate on the center of the absorbent core in the width direction, and the shape of the front end part of the absorbent core is such that the center in the width direction is easy to project toward the front side relative to the side part in the width direction. Hence, the region arranged to overlap the central region in the front-rear direction is easier to be subjected to the force directed from the absorbent core to the front side. By providing the duplicating region in the region, deformation due to the absorbent core is absorbed by the front end part of the absorbent body, thereby allowing deformation of the exterior body to be further suppressed.

According to one or more embodiments, the duplicating region is arranged to overlap, in the front-rear direction, the entire region of the absorbent core in the width direction.

By providing the duplicating region in the region arranged to overlap, in the front-rear direction, the absorbent core in the width direction, deformation due to the absorbent core is absorbed by the front end part of the absorbent body, thereby allowing deformation of the exterior body to be further suppressed.

According to one or more embodiments, the body non-bonding region is provided at a front end edge of the absorbent body.

The front end edge of the absorbent body is provided with both the body non-bonding region and a sheet non-bonding region, and hence the absorbent body is easier to deform. The deformation due to the absorbent core is absorbed by the front end edge of the absorbent body, thereby making it difficult for the absorbent body to push up the front exterior body and allowing deformation of the exterior body to be further suppressed.

According to one or more embodiments, the sheet non-bonding region extends toward the crotch region side relative to the body non-bonding region.

The liquid-impermeable sheet is often higher in rigidity than the liquid-permeable sheet, and the sheet non-bonding region is more likely to have an effect of lowering the rigidity than the body non-bonding region has. Since the sheet non-bonding region extends to the crotch region side relative to the body non-bonding region, it is easier to obtain an effect of absorbing deformation of the absorbent core by deformation of the absorbent body.

According to one or more embodiments, the sheet non-bonding region extends outside in the width direction relative to the body non-bonding region.

Since the sheet non-bonding region extends outside in the width direction relative to the body non-bonding region, it is possible to reduce rigidity over the entire region in the width direction of the body non-bonding region. The deformation of the exterior body can be further suppressed by the deformation of the duplicating region at the front end part of the absorbent body.

According to one or more embodiments, the body sheet has a first body sheet arranged on a skin surface side relative to the liquid-impermeable sheet, and a second body sheet arranged on the non-skin surface side relative to the liquid-impermeable sheet, and, in the sheet non-bonding region, the liquid-impermeable sheet is not bonded to the first body sheet and is not bonded to the second body sheet.

Since the liquid-impermeable sheet is not bonded to the first body sheet and the second body sheet, the liquid-impermeable sheet is easier to deform. Hence, the front end part of the absorbent body becomes easier to deform, thereby suppressing the deformation that the exterior body floats, and allowing the position shift of the exterior body in the front waistline region to be suppressed.

According to one or more embodiments, the liquid-impermeable sheet and the body sheet are arranged to straddle a region overlapping the absorbent core in the thickness direction and the front end part and are arranged to sandwich the absorbent core in the thickness direction, the crotch region side relative to the sheet non-bonding region is provided with a sheet bonding region in which the liquid-impermeable sheet and the body sheet are bonded, and the inner end edge of the sheet non-bonding region on the crotch region side is arranged on the front side relative to the absorbent core.

Since the inner end edge of the sheet non-bonding region on the crotch region side is located on the front side relative to the absorbent core, the sheet bonding region is provided on the front side relative to the absorbent core. It is possible to suppress leakage of an absorptive material constituting the absorbent core to the outside of the absorbent body by the region where the liquid-impermeable sheet and the body sheet are bonded.

According to one or more embodiments, a cover sheet is arranged on the skin surface side of the absorbent body, and the sheet non-bonding region is arranged to overlap, in the thickness direction, at least a part of a cover non-bonding region where the absorbent body and the cover sheet are not bonded.

The cover sheet located on the skin surface side of the wearer adheres closely to the skin, and the cover sheet may hardly deform. The front end part of the absorbent body is not bonded to the cover sheet and is easy to move relative to the cover sheet. Even when the cover sheet hardly deforms, the front end part of the absorbent body is easy to deform, thereby suppressing the deformation that the exterior body floats, and allowing the position shift of the exterior body in the front waistline region and the rear waistline region to be suppressed.

An absorbent article according to one or more embodiments is an absorbent article having a front-rear direction, a width direction orthogonal to the front-rear direction, a front waistline region, a rear waistline region, a crotch region arranged between the front waistline region and the rear waistline region, an absorbent body arranged to straddle the crotch region, the front waistline region, and the rear waistline region, and a front exterior body arranged in the front waistline region on a non-skin surface side of the absorbent body, wherein the absorbent body has an absorbent core and a front end part extending to the front side relative to the absorbent core, the front end part of the absorbent body is provided with an overlapping region where a first sheet material and a second sheet material overlap in a thickness direction, and a front end edge of the overlapping region is provided with a sheet non-bonding region where the first sheet material is not bonded to the second sheet material.

The front end edge of the overlapping region provided at the front end part of the absorbent body is provided with the sheet non-bonding region. The rigidity of the front end part of the absorbent body is lower than that of the configuration in which the first sheet material is bonded to the second sheet material. When a force moving in the front-rear direction is applied to the absorbent core, the front end part of the absorbent body deforms to absorb the force, thereby making it difficult for the force directed from the absorbent body to the front side to be transmitted to the exterior body, and making it difficult for the absorbent body to push up the exterior body. Hence, deformation such that the front exterior body floats is suppressed, and position shift of the front exterior body can be suppressed.

According to one or more embodiments, the sheet non-bonding region is arranged to overlap the absorbent core in the front-rear direction.

The region arranged to overlap the absorbent core in the front-rear direction is easy to be subjected to a force directed from the absorbent core to the front side. By providing the sheet non-bonding region in at least a part of the region, it is possible to make it further difficult for the force directed toward the front side to be transmitted from the absorbent body to the exterior body, and it is possible to suppress the position shift of the front exterior body.

According to one or more embodiments, the absorbent body has a central region which is a region obtained by dividing the total length of the absorbent core in the width direction into three equal parts and is located at the center of the absorbent core in the width direction, and the sheet non-bonding region is arranged to overlap the central region in the front-rear direction.

When the wearer moves his leg in the front-rear direction with the absorbent core sandwiched between the legs of the wearer, the force is easy to concentrate on the center of the absorbent core in the width direction, and the shape of the front end edge of the absorbent core is such that the center in the width direction is easy to project toward the front side relative to the side part in the width direction. Hence, the region arranged to overlap the central region in the front-rear direction is easier to be subjected to the force directed from the absorbent core to the front side. By providing the sheet non-bonding region in the region, it is possible to make it further difficult for the force directed from the absorbent body toward the front side to be transmitted to the front exterior body, and it is possible to suppress the position shift of the front exterior body.

According to one or more embodiments, the sheet non-bonding region is arranged to overlap, in the front-rear direction, the entire region of the absorbent core in the width direction.

By providing the sheet non-bonding region in the region arranged to overlap, in the front-rear direction, the entire region of the absorbent core in the width direction, it is possible to make it further difficult for the force directed from the absorbent body toward the front side to be transmitted to the front exterior body, and it is possible to suppress the position shift of the front exterior body.

According to one or more embodiments, at least the first sheet material of the first sheet material and the second sheet material is a liquid-impermeable sheet.

The liquid-impermeable sheet is constituted of a film or the like, and is often higher in rigidity than a sheet material which is a liquid-permeable sheet. Since the first sheet material, which is a liquid-impermeable sheet, is not bonded to the second sheet material, the rigidity of the front end part of the absorbent body is easy to be low, and it is possible to make it more difficult for the force to be transmitted from the absorbent body to the front exterior body.

According to one or more embodiments, the second sheet material is arranged on the skin surface side of the first sheet material, and the first sheet material and the second sheet material are arranged to straddle the region overlapping the absorbent core in the thickness direction and the front end part and are arranged to sandwich the absorbent core in the thickness direction.

The sheet material arranged to sandwich the absorbent core in the thickness direction is easier to receive the force from the absorbent core. Since the sheet non-bonding region is provided between the sheet materials arranged to sandwich the absorbent core, it is possible to make it further difficult for the force directed from the absorbent body toward the front side to be transmitted to the front exterior body, and it is possible to suppress the position shift of the front exterior body.

According to one or more embodiments, the second sheet material is arranged on the skin surface side of the first sheet material, a third sheet material located on the non-skin surface side of the first sheet material is arranged on the front end part of the absorbent body, and, in the sheet non-bonding region, the first sheet material is not bonded to the second sheet material and is not bonded to the third sheet material.

In the sheet non-bonding region, the three layers of the first sheet material, the second sheet material, and the third sheet material are not bonded to one another. Hence, the rigidity of the front end part of the absorbent body is easy to be low, and it is possible to make it more difficult for the force to be transmitted from the absorbent body to the front exterior body.

According to one or more embodiments, the first sheet material and the second sheet material are arranged to sandwich the absorbent core in the thickness direction, and the length in the front-rear direction of the region where the first sheet material is not bonded to the second sheet material is longer than the length in the front-rear direction of the region where the first sheet material is not bonded to the third sheet material.

The first sheet material and the second sheet material arranged to sandwich the absorbent core in the thickness direction are easy to be subjected to the force from the absorbent core. Since the length in the front-rear direction of the region where the first sheet material is not bonded to the second sheet material is relatively long, it is possible to make it further difficult for the force directed from the absorbent body toward the front side to be transmitted to the front exterior body, and it is possible to suppress the position shift of the front exterior body.

According to one or more embodiments, a cover sheet is arranged on the skin surface side of the absorbent body and covers the front end edge of the absorbent body, and the cover sheet is arranged to overlap at least a part of the sheet non-bonding region in the thickness direction.

The front end part of the absorbent body is provided with the sheet non-bonding region where the sheet materials are not bonded together, and there is a risk that the front end edge of the sheet material touches the skin. By covering the sheet non-bonding region with the cover sheet, the front end edge of the sheet material hardly touches the skin, and irritation to the skin can be suppressed.

According to one or more embodiments, the cover sheet is arranged to overlap the entire region of the sheet non-bonding region.

It is possible to cover the entire region of the sheet non-bonding region with the cover sheet, and it is possible to cover not only the front end edge of the sheet material but also the entire region where the sheet material is easy to float in the thickness direction. Hence, irritation to the skin can be further suppressed.

According to one or more embodiments, a cover bonding region where the cover sheet is bonded to the absorbent body is arranged to overlap a part of the sheet non-bonding region in the thickness direction.

The rigidity is different between the region where the sheet non-bonding region and the cover bonding region overlap each other and the region where the sheet non-bonding region and the cover bonding region do not overlap each other. Gradual deformation occurs when the two regions receive the force from the absorbent core, and it is easier to absorb the force received from the absorbent core. Hence, it is possible to make it further difficult for the force directed from the absorbent body toward the front side to be transmitted to the front exterior body, and it is possible to suppress the position shift of the front exterior body.

According to one or more embodiments, the crotch region side relative to the sheet non-bonding region is provided with a sheet bonding region in which the first sheet material is bonded to the second sheet material, and a cover bonding region in which the cover sheet and the absorbent body are bonded is arranged to overlap the sheet bonding region in the thickness direction.

The region where the cover bonding region and the sheet bonding region overlap is higher in rigidity than the region where the cover bonding region and the sheet non-bonding region overlap or the region where the cover non-bonding region and the sheet non-bonding region overlap. Since the high rigidity region is provided on the crotch region side relative to the sheet non-bonding region, the force directed outward from the absorbent core in the front-rear direction can be dispersed to the sheet material and the cover sheet via the high rigidity region. It is easier to absorb the force received from the absorbent core by both the sheet material and the cover sheet. Hence, it is possible to make it further difficult for the force directed from the absorbent body toward the front side to be transmitted to the front exterior body, and it is possible to suppress the position shift of the front exterior body.

According to one or more embodiments, the front end edge of the overlapping region is provided with a body non-bonding region in which the absorbent body and the front exterior body are not bonded.

Since the front end part of the absorbent body is provided with the body non-bonding region, the rigidity of the front end part of the absorbent body is reduced as compared with the configuration in which the absorbent body and the exterior body are bonded. When a force moving forward is applied to the absorbent core, the front end part of the absorbent body deforms to easily absorb the force. The force directed from the absorbent body toward the front side becomes difficult to be transmitted to the exterior body, and it becomes difficult for the absorbent body to push up the exterior body. Hence, deformation such that the front exterior body floats is suppressed, and position shift of the front exterior body can be suppressed.

According to one or more embodiments, the sheet non-bonding region extends outside in the width direction relative to the body non-bonding region.

Since the sheet non-bonding region extends outside in the width direction relative to the body non-bonding region, it is possible to reduce rigidity over the entire region in the width direction of the body non-bonding region. The deformation of the front end part of the absorbent body makes it easier to suppress deformation such that the exterior body floats.

An absorbent article according to one or more embodiments is an absorbent article having a front-rear direction, a width direction orthogonal to the front-rear direction, a front waistline region, a rear waistline region, a crotch region arranged between the front waistline region and the rear waistline region, an absorbent body having an absorbent core and arranged to straddle the crotch region, the front waistline region, and the rear waistline region, a front exterior body arranged in the front waistline region to overlap the absorbent body in the thickness direction, a rear exterior body arranged in the front waistline region to overlap the absorbent body in the thickness direction, and a side bonded portion which bonds an outside part of the front exterior body in the width direction and an outside part of the rear exterior body in the width direction, wherein the front exterior body has a plurality of exterior sheets, and a front side relative to a front end edge of the absorbent body is provided with an exterior non-bonding region where at least two of the exterior sheets are not bonded together.

Since the exterior non-bonding region is provided on the front side relative to the front end edge of the absorbent body, the rigidity of the front side relative to the front end edge of the absorbent body becomes low as compared with the configuration in which the exterior sheets are all bonded together. When the front end edge of the absorbent body moves outward in the front-rear direction, the exterior non-bonding region deforms to absorb the force, and it is possible to suppress the front end edge of the absorbent body from moving to the non-skin surface side of the exterior body so as to roll up the exterior body. It is hence possible to suppress position shift of the exterior body in the front waistline region, and to continuously cover the abdomen of the wearer.

According to one or more embodiments, at least a part of the exterior non-bonding region is arranged to overlap the absorbent core in the front-rear direction.

The region arranged to overlap the absorbent core in the front-rear direction is easy to be subjected to a force directed from the absorbent core to the front side. By providing the exterior non-bonding region in at least a part of the region, when the front end edge of the absorbent body moves forward, the exterior non-bonding region deforms to absorb the force, and it is possible to further suppress position shift of the front exterior body.

According to one or more embodiments, the absorbent body has a central region which is a region obtained by dividing the total length of the absorbent core in the width direction into three equal parts and is located at the center of the absorbent core in the width direction, and the exterior non-bonding region is arranged to overlap the central region in the front-rear direction.

When the wearer moves his leg in the front-rear direction with the absorbent core sandwiched between the legs of the wearer, the force is easy to concentrate on the center of the absorbent core in the width direction, and the shape of the front end part of the absorbent core is such that the center in the width direction is easy to project toward the front side relative to the side part in the width direction. Hence, the region arranged to overlap the central region in the front-rear direction is easier to be subjected to the force directed from the absorbent core to the front side. By providing the sheet non-bonding region in the region, when the front end edge of the absorbent body moves forward, the exterior non-bonding region deforms to absorb the force, and it is possible to further suppress position shift of the exterior body in the front waistline region.

According to one or more embodiments, the exterior non-bonding region is arranged to overlap, in the front-rear direction, the entire region of the absorbent core in the width direction.

By providing the exterior non-bonding region in the region arranged to overlap, in the front-rear direction, the entire region of the absorbent core in the width direction, when the front end edge of the absorbent body moves forward, the exterior non-bonding region deforms to absorb the force, and it is possible to suppress position shift of the exterior body in the front waistline region.

According to one or more embodiments, the exterior sheet has an exterior non-skin-side sheet arranged on a non-skin surface side of the absorbent body, and a cover sheet covering the front end edge of the absorbent body and arranged on a skin surface side of the absorbent body, and the exterior non-bonding region is provided between the cover sheet and the exterior non-skin-side sheet.

The exterior non-skin-side sheet and the cover sheet are arranged to sandwich the absorbent body in the thickness direction, and are easier to receive the force from the absorbent body. By providing the exterior non-bonding region between the exterior non-skin-side sheet and the cover sheet, when the front end edge of the absorbent body moves forward, the exterior non-bonding region deforms to more easily absorb the force, and it is possible to further suppress position shift of the exterior body.

According to one or more embodiments, the exterior sheet has a plurality of exterior non-skin-side sheets arranged on the non-skin surface side of the absorbent body, and the exterior non-bonding region is provided between the exterior non-skin-side sheets.

Since the exterior non-bonding region is provided between the exterior non-skin-side sheets, when the front end edge of the absorbent body moves outward in the front-rear direction, the front exterior body deforms so as to be tucked to the non-skin surface side, thereby allowing the force to be absorbed. The force from the absorbent body is absorbed by the front exterior body, thereby allowing the position shift of the front exterior body to be suppressed.

According to one or more embodiments, the front side relative to the exterior non-bonding region is provided with an exterior bonding region in which the exterior sheets are bonded together.

The exterior bonding region has the exterior sheets bonded together, and is easy to be higher in rigidity than the exterior non-bonding region. In addition, the region in which the absorbent body is arranged is also easy to be higher in rigidity than the exterior non-bonding region. The exterior non-bonding region is sandwiched in the front-rear direction by a high rigidity region, and further deforms when the front end edge of the absorbent body moves toward the front side, thereby becoming easy to absorb the force. It is hence possible to further suppress position shift of the front exterior body.

According to one or more embodiments, the length of the exterior bonding region in the front-rear direction is longer than the length of the exterior non-bonding region in the front-rear direction.

The exterior bonding region is higher in rigidity than the exterior non-bonding region, and the length in the front-rear direction is less easy to become short. By providing a relatively long length of the exterior bonding region in the front-rear direction, it is easy to secure a region covering the waistline by the front exterior body.

According to one or more embodiments, the absorbent body has a front end part extending to the front side relative to the absorbent core, the exterior sheet has a cover sheet covering the front end edge of the absorbent body and arranged on a skin surface side of the absorbent body, and the front end part of the absorbent body is provided with a cover non-bonding region in which the absorbent body and the cover sheet are not bonded.

The cover non-bonding region is lower in rigidity than the region where the absorbent body and the exterior body are bonded. By providing the cover non-bonding region, it becomes difficult for the force to be transmitted from the absorbent body to the exterior body, and it is possible to reduce the force transmitted to the region on the front side relative to the front end edge of the absorbent body. The deformation of the front exterior body is suppressed, and it is easy to continuously cover the waistline by the front-side exterior pair.

According to one or more embodiments, the cover non-bonding region is continuous with the exterior non-bonding region in the front-rear direction.

Since the cover non-bonding region and the exterior non-bonding region are continuous in the front-rear direction, a region deforming by the force from the absorbent body can be secured long near the front end edge of the absorbent body. It becomes easier for the front exterior body to absorb the force from the absorbent body, and it is possible to further suppress the position shift of the front exterior body.

According to one or more embodiments, the length of the exterior non-bonding region in the front-rear direction is longer than the length of the cover non-bonding region in the front-rear direction.

As compared with a configuration in which the length of the cover non-bonding region in the front-rear direction is longer than that of the exterior non-bonding region, a region deforming by the force from the absorbent body can be secured in the front exterior body, and it is possible to further suppress position shift of the front exterior body.

According to one or more embodiments, the length of the cover non-bonding region in the front-rear direction is longer than the length of the exterior non-bonding region in the front-rear direction.

As compared with a configuration in which the length of the exterior non-bonding region in the front-rear direction is longer than that of the cover non-bonding region, a region deforming by the force from the absorbent body can be secured in the cover sheet, and it is possible to further suppress position shift of the front exterior body.

According to one or more embodiments, the absorbent body has a front end part extending to the front side relative to the absorbent core, the exterior sheet has an exterior non-skin-side sheet arranged on a non-skin surface side of the absorbent body, and the front end part of the absorbent body is provided with a body non-bonding region in which the absorbent body and the exterior non-skin-side sheet are not bonded.

The body non-bonding region is lower in rigidity than the region where the absorbent body and the exterior non-skin-side sheet are bonded. By providing the body non-bonding region, it becomes difficult for the force to be transmitted from the absorbent body to the exterior body, and it is possible to reduce the force transmitted to the region on the front side relative to the front end edge of the absorbent body. In addition, since the non-skin surface side of the absorbent body is provided with the body non-bonding region, the front exterior body is easy to deform so as to be tucked to the non-skin surface side. It is possible for the front exterior body to further absorb the force from the absorbent body, and it is possible to suppress the position shift of the front exterior body.

According to one or more embodiments, the body non-bonding region is continuous with the exterior non-bonding region in the front-rear direction.

Since the body non-bonding region and the exterior non-bonding region are continuous in the front-rear direction, a region deforming by the force from the absorbent body can be secured long near the front end edge of the absorbent body. It becomes easier for the front exterior body to absorb the force from the absorbent body, and it is possible to further suppress the position shift of the front exterior body.

According to one or more embodiments, the length of the exterior non-bonding region in the front-rear direction is longer than the length of the body non-bonding region in the front-rear direction.

As compared with a configuration in which the length of the body non-bonding region in the front-rear direction is longer than the length of the exterior non-bonding region, it is possible to secure a region deforming by the force from the absorbent body in the front exterior body, and it is possible to further suppress position shift of the front exterior body.

According to one or more embodiments, the length of the body non-bonding region in the front-rear direction is longer than the length of the exterior non-bonding region in the front-rear direction.

Since the body non-bonding region is provided on the non-skin surface side of the absorbent body, the front exterior body is easy to deform so as to be tucked to the non-skin surface side. It is possible for the front exterior body to further absorb the force from the absorbent body, and it is possible to suppress the position shift of the front exterior body.

According to one or more embodiments, the absorbent body has a front end part extending to the front side relative to the absorbent core, the exterior sheet has an exterior non-skin-side sheet arranged on a non-skin surface side of the absorbent body, and a cover sheet covering the front end edge of the absorbent body and arranged on the skin surface side of the absorbent body, the front end part of the absorbent body is provided with a cover non-bonding region where the absorbent body and the cover sheet are not bonded, and a body non-bonding region where the absorbent body and the exterior non-skin-side sheet are not bonded, and the length of the body non-bonding region in the front-rear direction is longer than the length of the cover non-bonding region in the front-rear direction.

The body non-bonding region is arranged on the non-skin surface side of the absorbent body, and the cover non-bonding region is arranged on the skin surface side of the absorbent body. Since the length of the body non-bonding region in the front-rear direction is relatively long, the front exterior body is easy to deform so as to be tucked to the non-skin surface side. It is possible for the front exterior body to further absorb the force from the absorbent body, and it is possible to suppress the position shift of the front exterior body.

(2) Absorbent Article According to One or More Embodiments

The absorbent article according to one or more embodiments will be described below with reference to the drawings. It is to be noted that in the following drawings, identical or similar parts are denoted by the identical or similar reference numerals. However, it is to be noted that the drawings are schematic, and the proportions of each dimension are different from the actual ones. Accordingly, specific dimensions should be determined in consideration of the following explanation. It is also possible to include parts having different dimensional relationships and proportions among the drawings.

Figure 2:
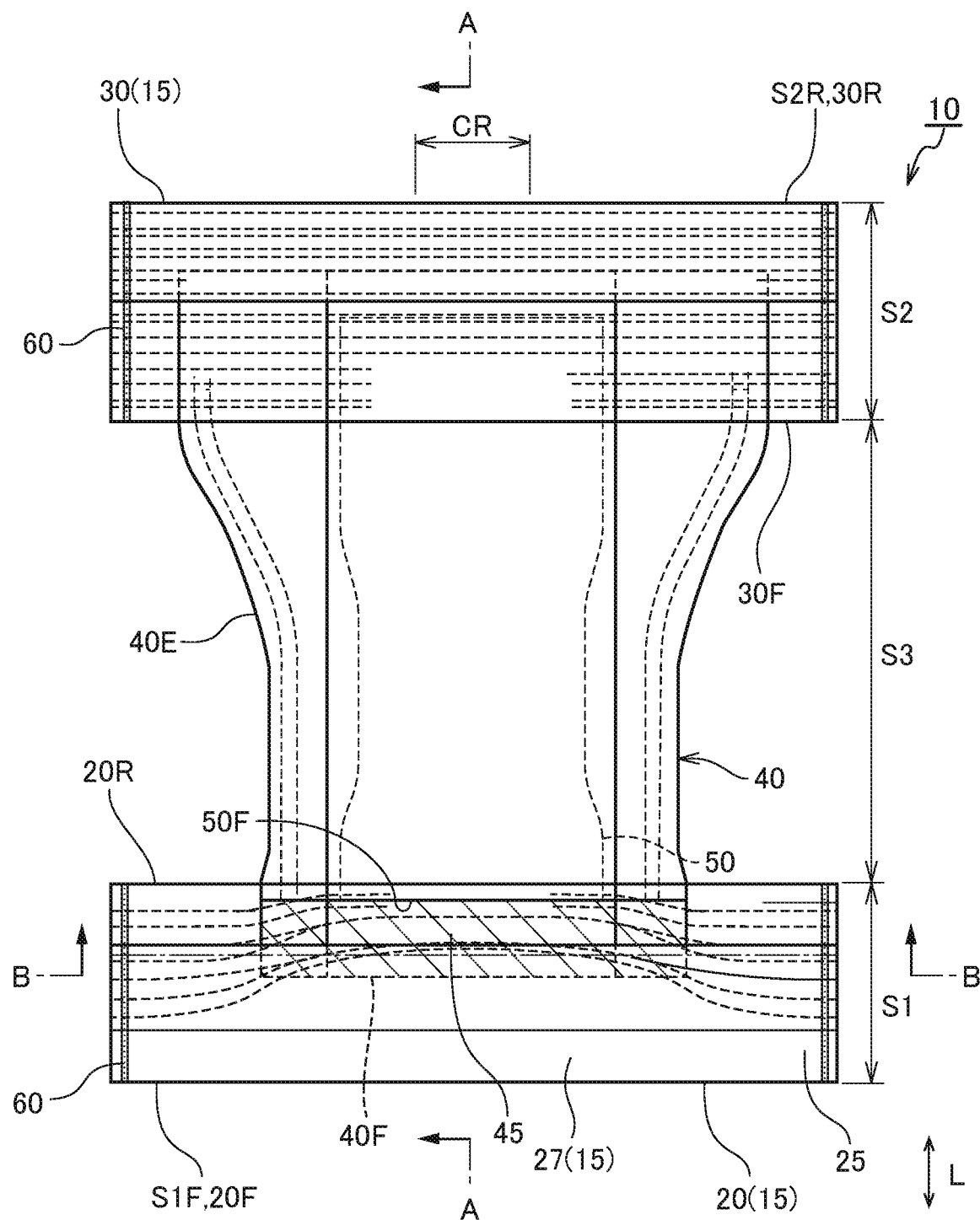
FIG. 2 is a plan view of the absorbent article according to one or more embodiments.
Figure 3:
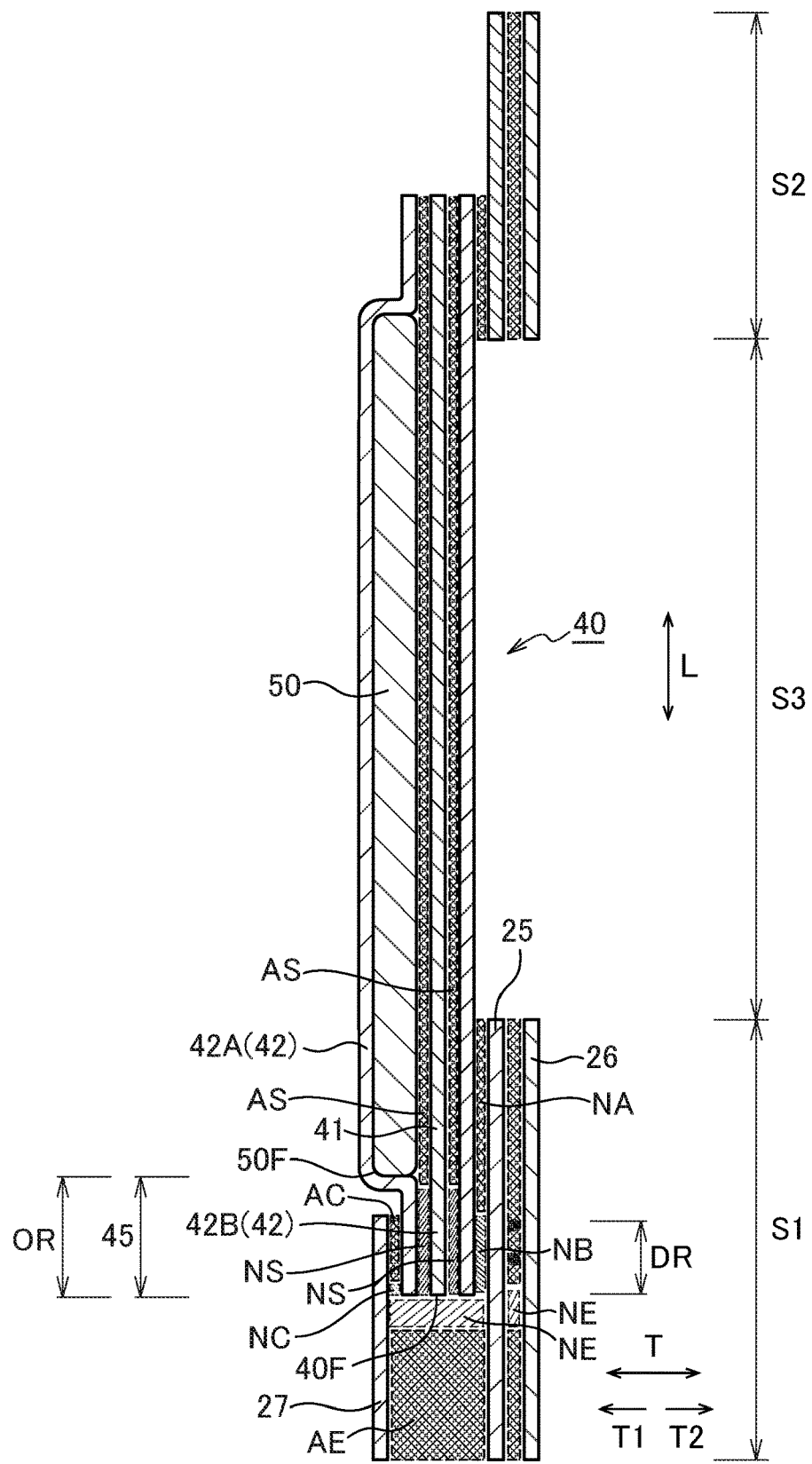
FIG. 3 is a cross-sectional view along a cross section A-A of the absorbent article shown in FIG. 2.
Figure 4:
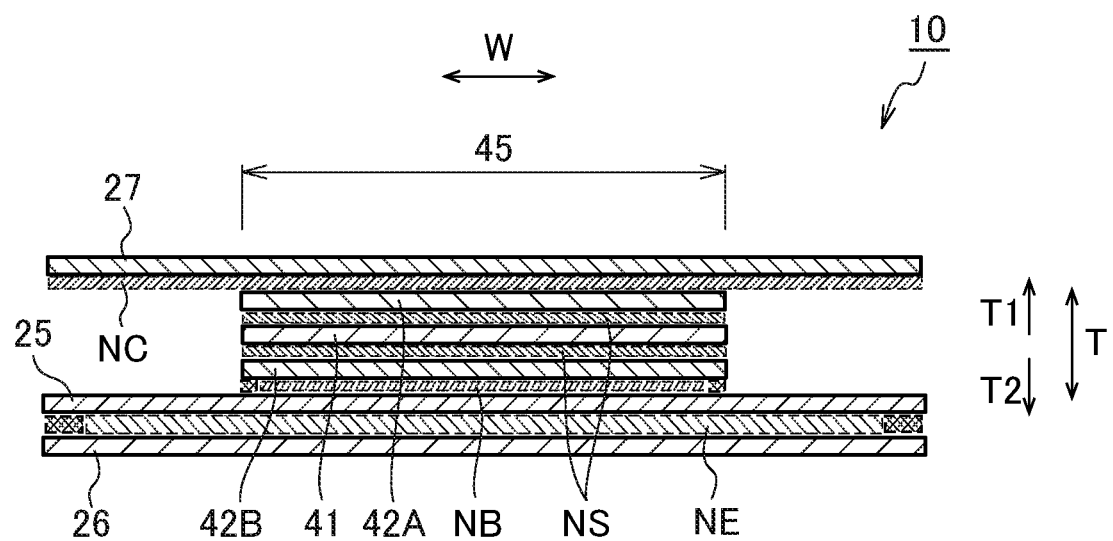
FIG. 4 is a cross-sectional view along a cross section B-B of the absorbent article shown in FIG. 2.

The absorbent article may also be a tape type or an underpants type. The absorbent article may be a disposable diaper or a shorts type sanitary napkin. The absorbent article of one or more embodiments is an underpants-type disposable diaper. FIG. 1 is a schematic front view of an absorbent article 10 according to one or more embodiments of the present invention. FIG. 2 is a schematic plan view of the absorbent article 10 according to one or more embodiments of the present invention. The schematic plan view shown in FIG. 2 shows a stretched state in which the absorbent article 10 is stretched to a state in which no wrinkles are formed in a state where a side bonded portion 60 described later is developed. FIG. 3 is a cross-sectional view along a line A-A shown in FIG. 2, and FIG. 4 is a cross-sectional view along a line B-B shown in FIG. 2.

The absorbent article 10 has a front-rear direction L and a width direction W that are orthogonal to each other. The front-rear direction L is defined by the direction extending to a front side of the human body and a rear side of the human body. In other words, the front-rear direction L is a direction extending back and forth of the developed absorbent article 10. In addition, the absorbent article 10 has a thickness direction T orthogonal to both the front-rear direction L and the width direction W.

The absorbent article 10 has a front waistline region S1, a rear waistline region S2, and a crotch region S3. The front waistline region S1 is a region facing the front waistline (abdomen) of the wearer. The rear waistline region S2 is a region facing the rear waistline (back) of the wearer. The crotch region S3 is a region located at the crotch of the wearer and arranged between the front waistline region S1 and the rear waistline region S2.

In one or more embodiments of the present invention, the absorbent article 10 may have an exterior body 15 and an absorbent body 40. The exterior body 15 overlaps the absorbent body 40 in the thickness direction and is arranged in at least the front waistline region S1. The exterior body 15 may have a front exterior body 20 and a rear exterior body 30. The front exterior body 20 is an exterior body arranged on a non-skin surface side T2 of the absorbent body 40 in the front waistline region S1. The rear exterior body 30 is an exterior body separated from the front exterior body 20 in the front-rear direction L and arranged on the non-skin surface side T2 of the absorbent body 40 in the rear waistline region S2.

The exterior body 15 may have a cover sheet 27 arranged on a skin surface side T1 of the absorbent body 40. The cover sheet 27 may be provided on the skin surface side T1 of the absorbent body 40 in the front waistline region.

The crotch region S3 is a region in which a leg opening 72 (See FIG. 1) described later is formed. A boundary on the crotch region side of the front waistline region S1 is a front end edge of the leg opening 72, and a boundary on the crotch region side of the rear waistline region S2 is a rear end edge of the leg opening 72. In one or more embodiments, the exterior body 15 may be configured by integrating the front exterior body 20 and the rear exterior body 30 and provided from the front waistline region S1 to the rear waistline region S2.

The front exterior body 20 and the rear exterior body 30 may be constituted of a sheet such as a nonwoven fabric. The front exterior body 20 may have a plurality of exterior sheets. The exterior sheet may have a first exterior sheet 25 and a second exterior sheet 26 located on the non-skin surface side T2 of the first exterior sheet 25. The cover sheet 27 may be constituted of a sheet such as a nonwoven fabric. The cover sheet 27 may be constituted by a part in which at least one of the first exterior sheet 25 and the second exterior sheet 26, which constitute the front exterior body 20, is folded back to the skin surface side T1, or may be constituted by a sheet separate from the first exterior sheet 25 and the second exterior sheet 26.

As shown in FIG. 1, a side bonded portion 60 in which an outside part of the front waistline region S1 in the width direction W and an outside part of the rear waistline region S2 in the width direction W are bonded may be provided. FIG. 2 shows a state in which the bonding at the side bonded portion 60 is released and the absorbent article 10 is developed. The side bonded portion 60 may extend along the front-rear direction L in each of the front exterior body 20 and the rear exterior body 30.

It is to be noted that in one or more embodiments of the present invention, the outside part is a part occupying a certain range in a width direction W including an outer edge in the width direction W, and an outside edge is the outer edge in the width direction W. In one or more embodiments of the present invention, the inside part is a part occupying a certain range in the width direction W including an inner edge in the width direction W, and an inside edge is the inner edge in the width direction W. In addition, the front end part and the rear end part in one or more embodiments of the present invention are parts occupying a certain range in the front-rear direction L including the edge in the front-rear direction L, and the front end edge and the rear end edge are edges in the front-rear direction L. An outer end part includes the front end part and the rear end part, and an outer end edge includes the front end edge and the rear end edge.

As shown in FIG. 1, in a state where the side bonded portion 60 is formed, the absorbent article 10 is formed with a waistline opening 71 through which the waist of the wearer passes, and a pair of the leg openings 72 into which the legs of the wearer are inserted. The waistline opening 71 may be defined by a front end edge 20F of the front exterior body that is a front end edge S1F of the front waistline region S1 and a rear end edge 30R of the rear exterior body 30 that is a rear end edge S2R of the rear waistline region S2. In addition, the leg opening 72 may be defined by a rear end edge 20R of the front exterior body 20 extending outward in the width direction W relative to the absorbent body 40, a front end edge 30F of the rear exterior body 30 extending outward in the width direction W relative to the absorbent body 40, and an outside edge 40E of the absorbent body 40 in the crotch region S3.

The absorbent body 40 is arranged to straddle the front exterior body 20 and the rear exterior body 30. That is, the absorbent body 40 extends over the front waistline region S1, the rear waistline region S2, and the crotch region S3. The absorbent body 40 may be configured as a separate body from the front exterior body 20 and the rear exterior body 30. The absorbent body 40 may have a region in which the front exterior body 20 or the rear exterior body 30 is arranged on the non-skin surface side T2, a region which does not overlap the exterior body 15 in the thickness direction T, and a region which is sandwiched in the thickness direction between the front exterior body 20 and the cover sheet.

The absorbent body 40 includes at least an absorbent core 50. The absorbent core 50 may include, for example, ground pulp or a superabsorbent polymer (SAP), or a mixture of them. The absorbent core 50 is arranged in at least the crotch region S3. In one or more embodiments, the absorbent core 50 may extend from the front waistline region S1 to the rear waistline region S2 in the front-rear direction L. The absorbent core 50 may be covered with a core wrap.

As shown in FIG. 2, the absorbent body 40 may have a front end part 45 extending to the front side relative to the absorbent core 50. The front end part 45 is a region between a front end edge 50F of the absorbent core 50 and a front end edge 40F of the absorbent body 40 in the front-rear direction L, and a region from one outside edge 40E of the absorbent body 40 to the other outside edge 40E in the width direction W. FIGS. 3 and 4 show the range of the front end part 45 in the front-rear direction and the range of the front end part 45 in the width direction. In addition, the absorbent body 40 may have a central region CR located at the center in the width direction W of the absorbent core 50. The central region CR is a region located at the center in the width direction W of the region obtained by dividing the total length of the absorbent core 50 in the width direction W into three equal parts.

As shown in FIGS. 3 and 4, the absorbent body 40 may include at least a liquid-impermeable sheet 41 and a body sheet 42 overlapping the liquid-impermeable sheet 41 in the thickness direction T. The liquid-impermeable sheet 41 and the body sheet 42 may be arranged in at least the front end part 45. The liquid-impermeable sheet 41 and the body sheet 42 may be arranged to straddle a region overlapping the absorbent core 50 and the front end part 45. The liquid-impermeable sheet 41 may be arranged on the non-skin surface side T2 relative to the absorbent core 50. The body sheet 42 may have a first body sheet 42A arranged on the skin surface side T1 relative to the liquid-impermeable sheet 41 and on the skin surface side T1 relative to the absorbent core 50, and a second body sheet 42B arranged on the non-skin surface side T2 relative to the liquid-impermeable sheet 41.

In the front end part 45 of the absorbent body 40 of one or more embodiments of the present invention, the first body sheet 42A, the liquid-impermeable sheet 41, and the second body sheet 42B are arranged in this order from the skin surface side T1 toward the non-skin surface side T2. In the region overlapping the absorbent core 50 of one or more embodiments of the present invention, the first body sheet 42A, the absorbent core 50, the liquid-impermeable sheet 41, and the second body sheet 42B are arranged in this order from the skin surface side T1 toward the non-skin surface side T2. The first body sheet 42A and the liquid-impermeable sheet 41 may be arranged to sandwich the absorbent core 50 in the thickness direction T.

The liquid-impermeable sheet 41 is only required to be liquid-impermeable, and may be constituted of, for example, a film. The liquid-impermeable sheet 41 may be constituted of a single sheet. Alternatively, the liquid-impermeable sheet 41 may be constituted of a laminated sheet in which a plurality of sheets are laminated to one another. In this case, at least one of the plurality of sheets may have liquid-impermeability.

The body sheet 42 is only required to be liquid-permeable, and may be constituted of, for example, a nonwoven fabric. The body sheet 42 may be constituted of a single sheet. Alternatively, the body sheet 42 may be constituted of a laminated sheet in which a plurality of sheets are laminated to one another.

The absorbent article thus configured has a bonding region and a non-bonding region. The bonding region includes a region where the exterior body 15 and the absorbent body 40 are bonded, a region where the liquid-impermeable sheet 41 and the body sheet 42 of the absorbent body 40 are bonded, a region where the exterior sheets of the exterior body are bonded together, and a region where the exterior sheet and the cover sheet are bonded. The non-bonding region includes a region where the exterior body 15 and the absorbent body 40 are not bonded, a region where the liquid-impermeable sheet 41 and the body sheet 42 of the absorbent body 40 are not bonded, a region where exterior sheets of the exterior body are not bonded together, and a region where the exterior sheet and the cover sheet are not bonded. Next, the bonding region and the non-bonding region of the absorbent article 10 will be described. It is to be noted that the non-bonding region in one or more embodiments of the present invention includes not only a region where no adhesive is applied but also a region where an adhesive is slightly applied but the members are not bonded via the adhesive.

The absorbent article 10 may have a sheet non-bonding region NS in which the liquid-impermeable sheet 41 and the body sheet 42 are not bonded. At least a part of the sheet non-bonding region NS may be provided at the front end part 45. The sheet non-bonding region NS may be provided in the entire region of the front end part 45 or may be provided in a part of the front end part 45. At least a part of the sheet non-bonding region NS is only required to be provided in an overlapping region OR. The sheet non-bonding region NS may be provided in a part of the overlapping region OR, may be provided in the entire region of the overlapping region OR, or may be provided in the entire region of the front end part 45.

The absorbent article 10 may have a body non-bonding region NB where the absorbent body 40 and the front exterior body 20 are not bonded. The body non-bonding region NB may be a region in which, among the sheets constituting the absorbent body 40, the sheet arranged to face the front exterior body 20 and the front exterior body 20 are not bonded. Specifically, in the form where the second body sheet 42B is arranged on the entire surface of the non-skin surface of the absorbent body 40, the body non-bonding region NB may be a region where the second body sheet 42B and the front exterior body 20 are not bonded. In the form where the second body sheet 42B and the liquid-impermeable sheet 41 are arranged on the non-skin surface of the absorbent body 40, the body non-bonding region NB may include a region in which the second body sheet 42B and the front exterior body 20 are not bonded, and a region in which the liquid-impermeable sheet 41 and the front exterior body 20 are not bonded. At least a part of the body non-bonding region NB may be provided at the front end part 45. The body non-bonding region NB may be provided in the entire region of the front end part 45 or may be provided in a part of the front end part 45.

The absorbent article 10 may have a duplicating region DR where the sheet non-bonding region NS and the body non-bonding region NB overlap. The duplicating region DR is a region where the sheet non-bonding region NS and the body non-bonding region NB overlap in the thickness direction T. At least a part of the duplicating region DR may be provided at the front end part 45. The duplicating region DR may be provided in the entire front end part 45, or may be provided in a part of the front end part 45.

Figure 5A:
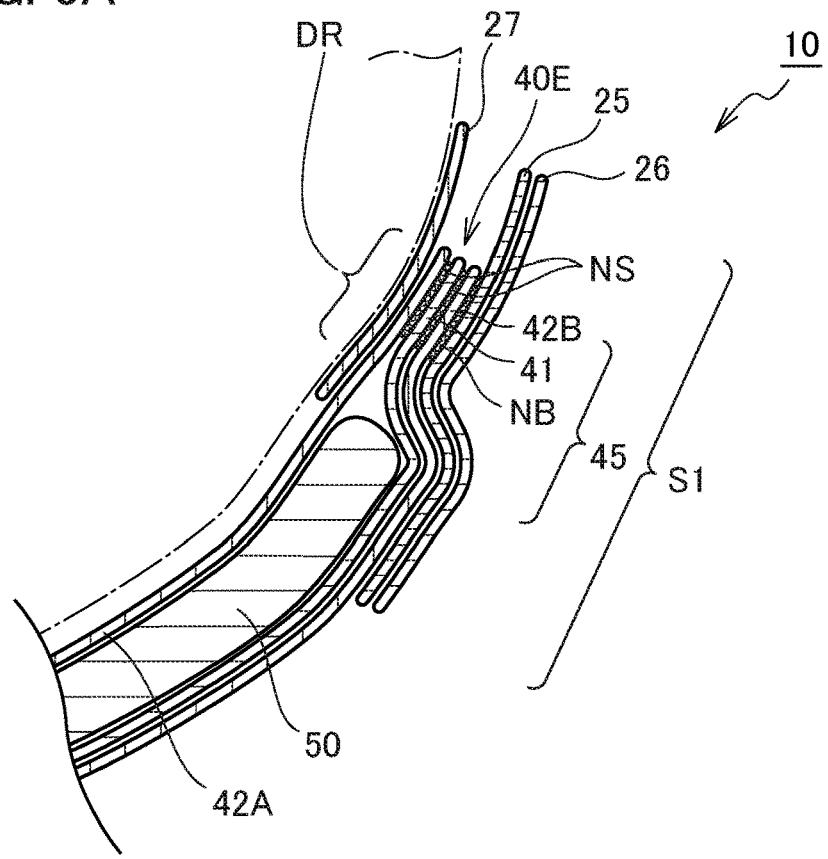
FIGS. 5A and 5B are views each schematically showing a cross section of the absorbent article in a mounted state according to one or more embodiments.
Figure 5B:
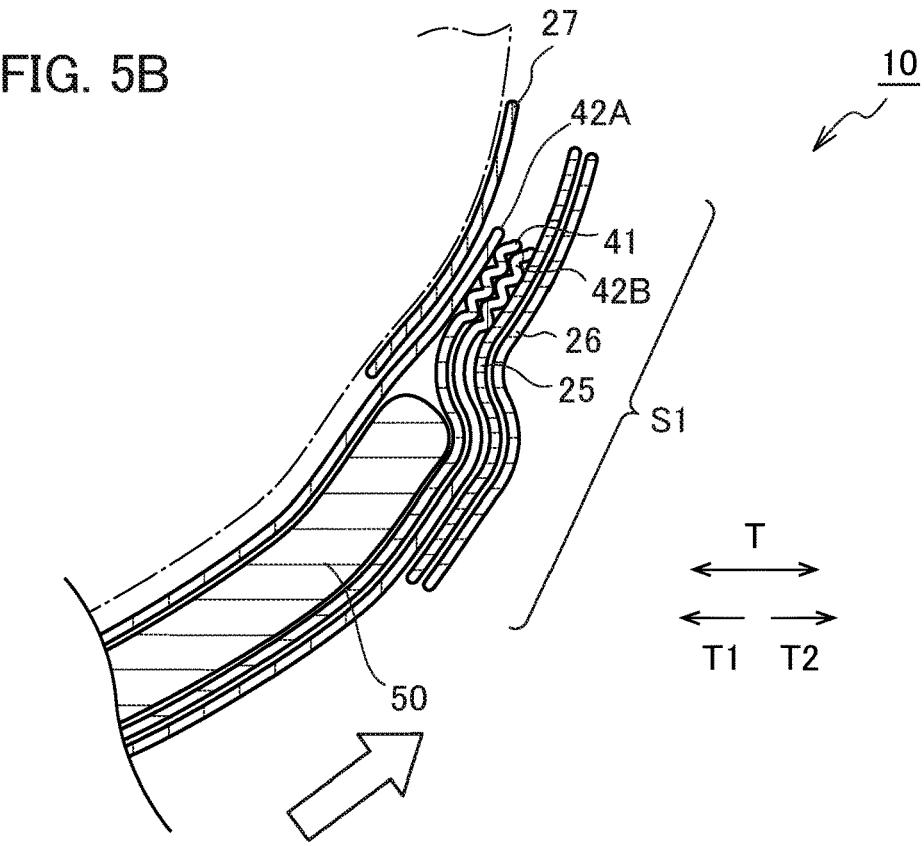
Figure 6A:
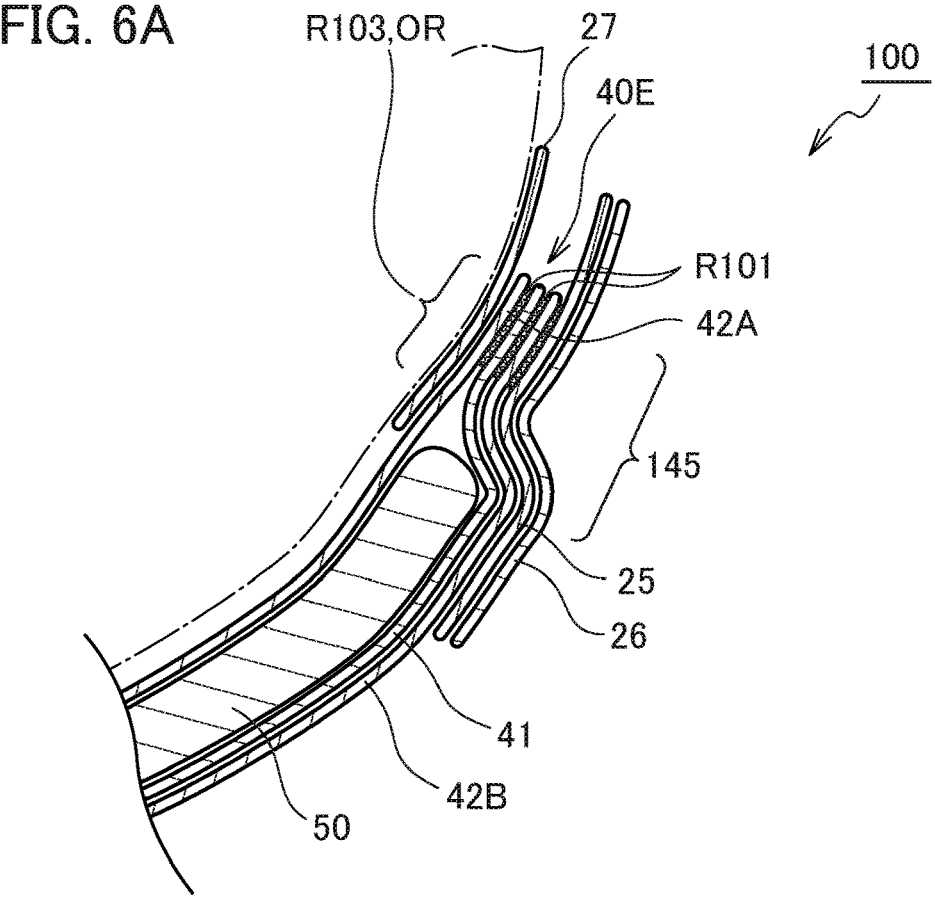
FIGS. 6A and 6B are views each schematically showing a cross section of an absorbent article in a mounted state according to a comparative example of one or more embodiments.
Figure 6B:
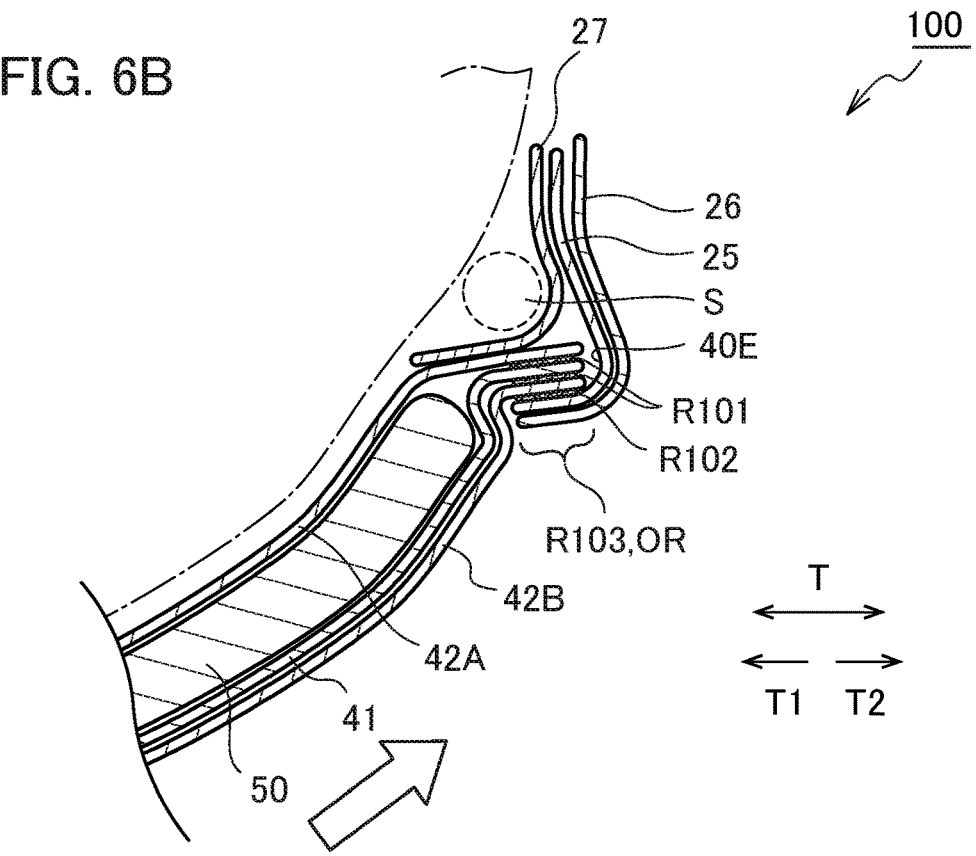

According to the absorbent article 10 thus configured, position shift of the exterior body 15 in the front waistline region S1 can be suppressed by the motion of the leg of the wearer. FIGS. 5A, 5B, 6A, and 6B are views each schematically showing a cross section of the absorbent article in a mounted state, and schematically show the abdomen of the wearer and the front waistline region of the absorbent article. The dashed lines shown in FIGS. 5A, 5B, 6A, and 6B indicate the body line of the wearer. FIGS. 5A and 5B each show a mounted state of the absorbent article according to one or more embodiments, and FIGS. 6A and 6B each show a mounted state of the absorbent article according to the comparative example. FIGS. 5A and 6A show a state before deformation, and FIGS. 5B and 6B show a deformed state in which the leg is moved back and forth.

As shown in FIGS. 6A and 6B, the front end part 145 of the absorbent article 100 according to the comparative example is not provided with the sheet non-bonding region NS and the body non-bonding region NB. The absorbent article 100 according to the comparative example is provided, at the front end part 145, with a bonding region R101 where the liquid-impermeable sheet 41 and the body sheet 42 are bonded, and a bonding region R102 where the absorbent body 40 and the front exterior body 20 are bonded. The front end part 145 is provided with a region R103 where the bonding region R101 and the bonding region R102 overlap in the thickness direction. Since the absorbent article 100 thus configured has the region R103 overlapping at the front end part 145, the rigidity of the front end part 145 is easy to become high. When the wearer moves his leg back and forth, a force moving in the front-rear direction L is applied to the absorbent core 50, and the front end part of the absorbent body 40 moves forward via the absorbent core 50. At this time, as shown in FIGS. 6A and 6B, a force is applied from the absorbent body 40 located on the skin surface side T1 toward the front exterior body 20 located on the non-skin surface side T2, and hence the front exterior body 20 floats away from the wearer and a space S is easy to be formed between the front end part 145 and the wearer. By floating away from the wearer, the front end edge S1F of the front waistline region S1 shifts to the crotch region S3 side, and the position of the front exterior body 20 may shift.

As shown in FIGS. 5A and 5B, the front end part 45 of the absorbent article 10 according to one or more embodiments is provided with the duplicating region DR in which the sheet non-bonding region NS and the body non-bonding region NB overlap. In the absorbent article 10 according to one or more embodiments, the front end part 45 is provided with a region where the sheets constituting the absorbent body 40 are not bonded together and the absorbent body 40 and the front exterior body 20 are not bonded. Since the front end part 45 of the absorbent body 40 is provided with the sheet non-bonding region NS, the rigidity of the front end part 45 of the absorbent body 40 becomes lower than that of the configuration in which the liquid-impermeable sheet 41 and the body sheet 42 are bonded, and the front end part 45 of the absorbent body 40 is easy to deform. In particular, the liquid-impermeable sheet 41 is constituted of a film or the like, and is often higher in rigidity than a liquid-permeable sheet. The sheet non-bonding region NS can reduce the rigidity due to the liquid-impermeable sheet 41, and the front end part 45 of the absorbent body 40 becomes easy to deform.

In addition, since the front end part 45 of the absorbent body 40 is provided with the duplicating region DR, the duplicating region DR is easier to deform when a force moving forward is applied from the absorbent core 50. The deformation of the front end part 45 of the absorbent body 40 makes it difficult for the absorbent body 40 to push up the front exterior body 20. It is possible to suppress deformation such that the front exterior body 20 floats from the human body, to suppress position shift of the front exterior body 20, and to continuously cover the abdomen of the wearer.

The duplicating region DR may be provided in the entire front end part 45, or may be provided in a part of the front end part 45. The front end edge of the duplicating region DR may coincide with the front end edge 40F of the absorbent body 40 or may be located on the rear side relative to the front end edge 40F of the absorbent body 40. The rear end edge of the duplicating region DR may be located on the front side relative to the front end edge 50F of the absorbent core 50, may be located on the rear side relative to the front end edge 50F of the absorbent core 50, or may coincide with the front end edge 50F of the absorbent core 50. The outside edge of the duplicating region DR may coincide with the outside edge 40E of the absorbent body 40, or may be located inside the width direction W relative to the outside edge 40E of the absorbent body 40.

In one or more embodiments, at least a part of the duplicating region DR may be arranged to overlap the absorbent core 50 in the front-rear direction L. The region arranged to overlap the absorbent core 50 in the front-rear direction L is easy to be subjected to a force directed from the absorbent core 50 to the front side. By providing the duplicating region DR in at least a part of the region, deformation due to the absorbent core 50 is absorbed by the front end part 45 of the absorbent body 40, and position shift of the exterior body 15 in the front waistline region S1 can be suppressed.

In one or more embodiments, the duplicating region DR may be arranged to overlap the central region CR in the front-rear direction L. When the wearer moves his leg in the front-rear direction with the absorbent core 50 sandwiched between the legs of the wearer, the force is easy to concentrate on the center of the absorbent core 50 in the width direction W, and the shape of the front end part 45 of the absorbent core 50 is such that the center in the width direction W is easy to project toward the front side relative to the side part in the width direction W. Hence, the region arranged to overlap the central region CR in the front-rear direction L is easier to be subjected to the force directed from the absorbent core 50 to the front side. By providing the duplicating region DR in the region, deformation due to the absorbent core 50 is absorbed by the front end part 45 of the absorbent body 40, thereby allowing deformation of the exterior body 15 to be further suppressed.

In one or more embodiments, the duplicating region DR may be arranged to overlap, in the front-rear direction, the entire region in the width direction W of the absorbent core 50. By providing the duplicating region DR in the region arranged to overlap, in the front-rear direction, the absorbent core 50 in the width direction W, deformation due to the absorbent core 50 is absorbed by the front end part 45 of the absorbent body 40, thereby allowing deformation of the exterior body 15 to be further suppressed.

The front end edge of the body non-bonding region NB and the front end edge of the sheet non-bonding region NS may coincide with the front end edge 40F of the absorbent body 40, or may be located on the rear side relative to the front end edge 40F of the absorbent body 40. In one or more embodiments, the body non-bonding region NB and the sheet non-bonding region NS may be provided at the front end edge of the absorbent body 40. The front end edge of the absorbent body 40 is provided with both the body non-bonding region NB and a sheet non-bonding region NS, and hence the absorbent body is easier to deform. The deformation due to the absorbent core 50 is absorbed by the front end edge of the absorbent body 40, thereby making it difficult for the absorbent body 40 to push up the front exterior body 20 and allowing deformation of the exterior body 15 to be further suppressed.

The rear end edge of the body non-bonding region NB and the rear end edge of the sheet non-bonding region NS may be located on the front side relative to the front end edge 50F of the absorbent core 50, may be located on the rear side relative to the front end edge 50F of the absorbent core 50, or may coincide with the front end edge 50F of the absorbent core 50. The outside edge of the body non-bonding region NB and the outside edge of the sheet non-bonding region NS may coincide with the outside edge 40E of the absorbent body 40, or may be located inside the width direction W relative to the outside edge 40E of the absorbent body 40.

The absorbent article 10 may have a sheet bonding region AS in which the liquid-impermeable sheet 41 and the body sheet 42 are bonded on the crotch region side relative to the sheet non-bonding region NS. The sheet bonding region AS is adjacent to the sheet non-bonding region NS in the front-rear direction. The sheet bonding region AS is a region where sheets not bonded in the sheet non-bonding region NS are bonded together.

In a form where the sheet non-bonding region NS is provided between the sheets sandwiching the absorbent core 50 in the thickness direction and straddling the absorbent core 50 and the front end part 45, the inner end edge of the sheet non-bonding region NS on the crotch region side, i.e., the front end edge of the sheet bonding region AS may be arranged on the front side relative to the absorbent core 50. The inner end edge of the sheet non-bonding region NS on the crotch region side may be arranged on the front side relative to the absorbent core 50. Since the inner end edge of the sheet non-bonding region NS on the crotch region side is located on the front side relative to the absorbent core 50, the sheet bonding region AS is provided on the front side relative to the absorbent core 50. It is possible to suppress leakage of an absorptive material constituting the absorbent core 50 to the outside of the absorbent body 40 by the region where the liquid-impermeable sheet 41 and the body sheet are bonded.

The sheet non-bonding region NS may be any of a region where the liquid-impermeable sheet 41 is not bonded to the first body sheet 42A, a region where the liquid-impermeable sheet 41 is not bonded to the second body sheet 42B, and a region where the liquid-impermeable sheet 41 is not bonded to the first body sheet 42A and the second body sheet 42B. In one or more embodiments, in the sheet non-bonding region NS, the liquid-impermeable sheet 41 may not be bonded to the first body sheet 42A and may not be bonded to the second body sheet 42B. Since the liquid-impermeable sheet 41 is not bonded to the first body sheet and the second body sheet, the liquid-impermeable sheet 41 is easier to deform. Hence, the front end part 45 of the absorbent body 40 becomes easier to deform, thereby suppressing the deformation that the exterior body 15 floats, and allowing the position shift of the exterior body 15 in the front waistline region to be suppressed.

The positional relationship in the front-rear direction between the sheet non-bonding region NS and the body non-bonding region NB is not limited. The front end edge of the sheet non-bonding region NS may be on the front side relative to the front end edge of the body non-bonding region NB, or may be on the rear side relative to the front end edge of the body non-bonding region NB. The rear end edge of the sheet non-bonding region NS may be on the front side relative to the rear end edge of the body non-bonding region NB, or may be on the rear side relative to the rear end edge of the body non-bonding region NB. In one or more embodiments, the sheet non-bonding region NS may extend to the crotch region side relative to the body non-bonding region NB. The liquid-impermeable sheet 41 is often higher in rigidity than the liquid-permeable sheet, and the sheet non-bonding region NS is more likely to have an effect of lowering the rigidity than the body non-bonding region NB has. Since the sheet non-bonding region NS extends to the crotch region side relative to the body non-bonding region NB, it is easier to obtain an effect of absorbing deformation of the absorbent core 50 by deformation of the absorbent body 40.

The positional relationship in the width direction W between the sheet non-bonding region NS and the body non-bonding region NB is not limited. The outer end edge of the sheet non-bonding region NS may be outside relative to the outside edge of the body non-bonding region NB, or may be inside relative to the outside edge of the body non-bonding region NB. In one or more embodiments, the sheet non-bonding region NS may extend outside in the width direction W relative to the body non-bonding region NB. Since the sheet non-bonding region NS extends outside in the width direction relative to the body non-bonding region NB, it is possible to reduce rigidity over the entire region in the width direction of the body non-bonding region NB. The deformation of the exterior body can be further suppressed by the deformation of the duplicating region at the front end part of the absorbent body.

The absorbent article 10 may have a cover non-bonding region NC where the absorbent body 40 and the cover sheet 27 are not bonded, and a cover bonding region AC where the absorbent body 40 and the cover sheet 27 are bonded. The cover non-bonding region NC may be a region where, among the sheets constituting the absorbent body 40, a sheet arranged to face the cover sheet 27 and the cover sheet 27 are not bonded. The cover bonding region AC may be a region where, among the sheets constituting the absorbent body 40, a sheet arranged to face the cover sheet 27 and the cover sheet 27 are bonded. The cover non-bonding region NC is a region that is lower in rigidity than the region where the cover sheet 27 and the absorbent body 40 are bonded, and that is easy to deform.

The sheet non-bonding region NS may be arranged to overlap at least a part of the cover non-bonding region NC in the thickness direction. The front end part 45 of the absorbent body 40 is not bonded to the cover sheet and is easy to move with respect to the cover sheet. Even when the cover sheet located on the skin surface side of the wearer adheres closely to the skin, and the cover sheet may hardly deform, the front end part 45 of the absorbent body 40 is easy to deform, thereby suppressing the deformation that the exterior body 15 floats, and allowing the position shift of the exterior body 15 in the front waistline region and the rear waistline region to be suppressed.

In addition, the cover bonding region AC may be arranged to overlap a part of the sheet non-bonding region NS in the thickness direction. A region where the sheet non-bonding region NS and the cover bonding region AC overlap and a region where the sheet non-bonding region NS and the cover bonding region AC do not overlap may be provided. The region where the sheet non-bonding region NS and the cover bonding region AC overlap and the region where the sheet non-bonding region NS and the cover bonding region AC do not overlap are different in rigidity. Gradual deformation occurs when the two regions receive the force from the absorbent core 50, and it is easier to absorb the force received from the absorbent core 50. Hence, it is possible to make it further difficult for the force directed from the absorbent body 40 toward the front side to be transmitted to the front exterior body 20, and it is possible to suppress the position shift of the front exterior body 20.

The cover bonding region AC may be arranged to overlap the sheet bonding region AS in the thickness direction T. The region where the cover bonding region AC and the sheet bonding region AS overlap is higher in rigidity than the region where the cover bonding region AC and the sheet non-bonding region NS overlap or the region where the cover non-bonding region NC and the sheet non-bonding region NS overlap. Since the high rigidity region is provided on the crotch region side relative to the sheet non-bonding region NS, the force directed outward from the absorbent core 50 in the front-rear direction can be dispersed to the sheet material and the cover sheet 27 via the high rigidity region. It is easier to absorb the force received from the absorbent core 50 by both the sheet material and the cover sheet 27. Hence, it is possible to make it further difficult for the force directed from the absorbent body 40 toward the front side to be transmitted to the front exterior body 20, and it is possible to suppress the position shift of the front exterior body 20.

The absorbent article 10 may have an exterior non-bonding region NE. The exterior non-bonding region NE is a region where two of the sheets of the first exterior sheet 25, the second exterior sheet 26, and the cover sheet 27 are not bonded together. The exterior non-bonding region NE may be provided on the front side relative to the front end edge 40F of the absorbent body 40. Since the exterior non-bonding region is provided on the front side relative to the front end edge of the absorbent body, the rigidity of the front side relative to the front end edge of the absorbent body becomes low as compared with the configuration in which all the exterior sheets are bonded together. When the front end edge of the absorbent body moves outward in the front-rear direction, the exterior non-bonding region NE deforms to absorb the force, and it is possible to suppress the entire front exterior body from deforming. It is hence possible to suppress position shift of the exterior body in the front waistline region, and to continuously cover the abdomen of the wearer.

The front side relative to the exterior non-bonding region NE may be provided with an exterior bonding region AE where the exterior sheets are bonded together. The exterior bonding region AE may include a region where the cover sheet 27 is bonded to the exterior sheet and a region where the exterior sheets are bonded together. The exterior bonding region AE is easy to be higher in rigidity than the exterior non-bonding region NE. In addition, the region in which the absorbent body 40 is arranged is also easy to be higher in rigidity than the exterior non-bonding region NE. The exterior non-bonding region NE is sandwiched in the front-rear direction L by a high rigidity region, and further deforms when the front end edge 40F of the absorbent body 40 moves toward the front side, thereby becoming easy to absorb the force. It is hence possible to further suppress position shift of the front exterior body.

(3) Absorbent Article According to One or More Embodiments

The absorbent article according to one or more embodiments will be described below with reference to the drawings. It is to be noted that in the following explanation of one or more embodiments, the same components as those of the above embodiments are denoted by the same reference numerals and explanation thereof is omitted.

Figure 7A:
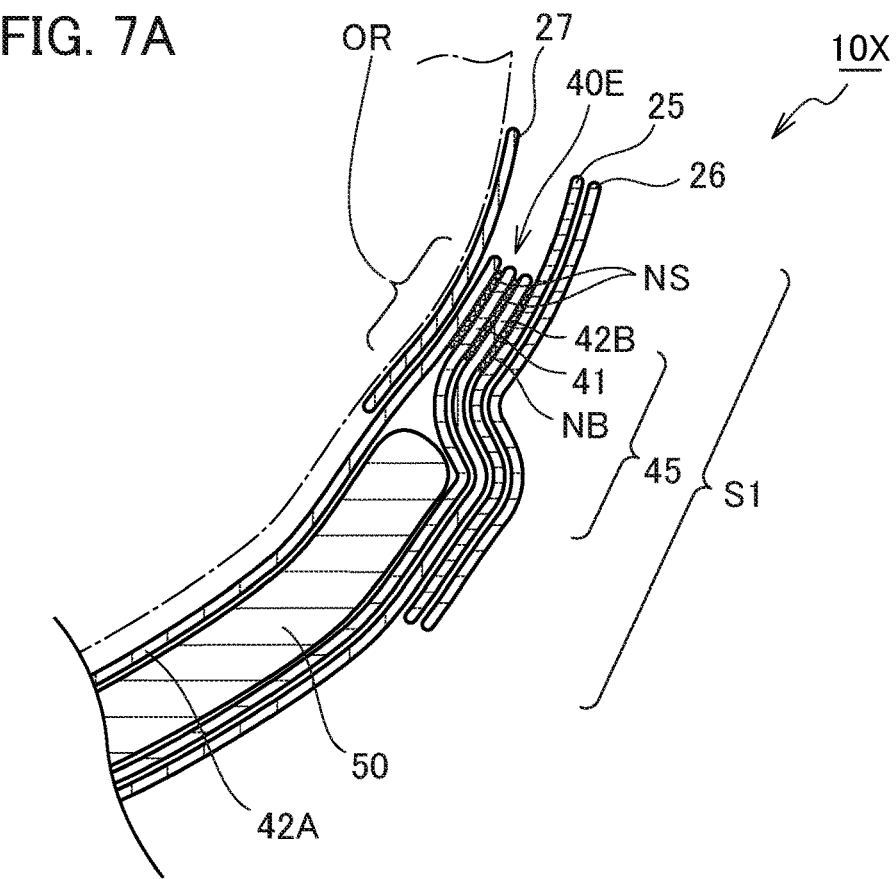
FIGS. 7A and 7B are views each schematically showing a cross section of an absorbent article in a mounted state according to one or more embodiments.
Figure 7B:
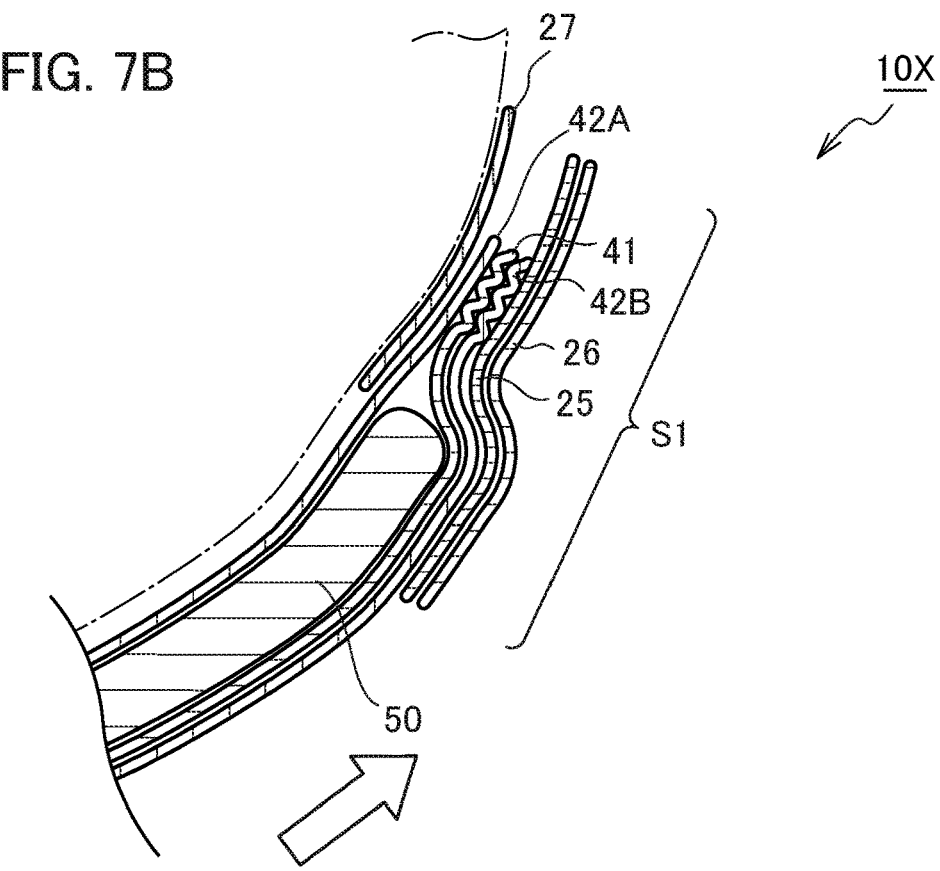

In an absorbent article 10X according to one or more embodiments, the plane and the cross section shown in FIGS. 1 to 4 are same as those of the above embodiments. FIGS. 7A and 7B are views each schematically showing a cross section of the absorbent article according to one or more embodiments in a mounted state, and schematically shows the abdomen of the wearer and the front waistline region of the absorbent article. FIG. 7A shows a state before deformation, and FIG. 7B shows a deformed state in which the leg is moved back and forth.

In one or more embodiments, the liquid-impermeable sheet 41, the first body sheet 42A, and the second body sheet 42B constitute a first sheet material and a second sheet material of one or more embodiments. Specifically, the liquid-impermeable sheet 41 may constitute the first sheet material and the first body sheet 42A or the second body sheet 42B may constitute the second sheet material, the first body sheet 42A may constitute the first sheet material and the liquid-impermeable sheet 41 or the second body sheet 42B may constitute the second sheet material, or the second body sheet 42B may constitute the first sheet material and the liquid-impermeable sheet 41 or the first body sheet 42A may constitute the second sheet material.

The front end part 45 of the absorbent body 40 may be provided with the overlapping region OR in which the first sheet material and the second sheet material overlap in the thickness direction. The overlapping region OR may be a region where at least two of the sheet materials of the liquid-impermeable sheet 41, the first body sheet 42A, and the second body sheet 42B overlap in the thickness direction. The overlapping region OR may also be a region where the liquid-impermeable sheet 41, the first body sheet 42A, and the second body sheet 42B overlap in the thickness direction. At least a part of the overlapping region OR may be provided at the front end part 45. The overlapping region OR may be provided in the entire region of the front end part 45 or may be provided in a part of the front end part 45.

According to the absorbent article 10X thus configured, position shift of the exterior body 15 in the front waistline region S1 can be suppressed by the motion of the leg of the wearer. FIGS. 7A and 7B are views each schematically showing a cross section of the absorbent article according to one or more embodiments in a mounted state, and schematically shows the abdomen of the wearer and the front waistline region of the absorbent article. FIG. 7A shows a state before deformation, and FIG. 7B shows a deformed state in which the leg is moved back and forth.

As shown in FIGS. 6A and 6B, the front end part 145 of the absorbent article 100 according to the comparative example is provided with the overlapping region OR, but the front end edge of the overlapping region OR is not provided with the sheet non-bonding region NS. The absorbent article 100 according to the comparative example is provided with the bonding region R101 where the liquid-impermeable sheet 41 and the body sheet 42 are bonded at the front end edge of the overlapping region OR. Since in the absorbent article 100 thus configured, the liquid-impermeable sheet 41 and the body sheet 42 are bonded at the front end edge of the overlapping region OR, the rigidity of the front end part 145 is easy to become high. When the wearer moves his leg back and forth, a force moving in the front-rear direction L is applied to the absorbent core 50, and the front end part of the absorbent body 40 moves forward via the absorbent core 50. At this time, as shown in FIGS. 6A and 6B, a force is applied from the absorbent body 40 located on the skin surface side T1 toward the front exterior body 20 located on the non-skin surface side T2, and hence the front exterior body 20 floats away from the wearer and a space S is easy to be formed between the front end part 145 and the wearer. By floating away from the wearer, the front end edge S1F of the front waistline region S1 shifts to the crotch region S3 side, and the position of the front exterior body 20 may shift.

As shown in FIGS. 7A and 7B, the front end part 45 of the absorbent article 10X according to one or more embodiments is provided with the overlapping region OR, and the front end edge of the overlapping region OR is provided with the sheet non-bonding region NS. In the absorbent article 10X according to one or more embodiments, the first sheet and the second sheet constituting the absorbent body 40 are not bonded at the front end edge of the overlapping region OR. The rigidity of the front end part 45 of the absorbent body becomes lower than that of the configuration where the first sheet material is bonded to the second sheet material. The overlapping region OR is easier to deform when a force moving forward is applied from the absorbent core 50. The deformation of the overlapping region OR of the absorbent body 40 makes it difficult for the absorbent body 40 to push up the front exterior body 20. It is possible to suppress deformation such that the front exterior body 20 floats from the human body, to suppress position shift of the front exterior body 20, and to continuously cover the abdomen of the wearer.

The sheet non-bonding region NS may be provided in the entire region of the front end part 45 or may be provided in a part of the front end part 45. The front end edge of the sheet non-bonding region NS may coincide with the front end edge 40F of the absorbent body 40. In one or more embodiments, at least a part of the sheet non-bonding region NS may be arranged to overlap the absorbent core 50 in the front-rear direction L. The region arranged to overlap the absorbent core 50 in the front-rear direction L is easy to be subjected to a force directed from the absorbent core 50 to the front side. By providing the sheet non-bonding region NS in at least a part of the region, deformation due to the absorbent core 50 is absorbed by the front end part 45 of the absorbent body 40, and position shift of the exterior body 15 in the front waistline region S1 can be suppressed.

In one or more embodiments, the sheet non-bonding region NS may be arranged to overlap the central region CR in the front-rear direction L. When the wearer moves his leg in the front-rear direction with the absorbent core 50 sandwiched between the legs of the wearer, the force is easy to concentrate on the center of the absorbent core 50 in the width direction W, and the shape of the front end part 45 of the absorbent core 50 is such that the center in the width direction W is easy to project toward the front side relative to the side part in the width direction W. Hence, the region arranged to overlap the central region CR in the front-rear direction is easier to be subjected to the force directed from the absorbent core 50 to the front side. By providing the sheet non-bonding region NS in the region, deformation due to the absorbent core 50 is absorbed by the front end part 45 of the absorbent body 40, thereby allowing deformation of the exterior body 15 to be further suppressed.

In one or more embodiments, the sheet non-bonding region NS may be arranged to overlap, in the front-rear direction, the entire region in the width direction W of the absorbent core 50. By providing the sheet non-bonding region NS in the region arranged to overlap, in the front-rear direction, the absorbent core 50 in the width direction W, deformation due to the absorbent core 50 is absorbed by the front end part 45 of the absorbent body 40, thereby allowing deformation of the exterior body 15 to be further suppressed.

At least the first sheet material of the first sheet material and the second sheet material that are not bonded in the sheet non-bonding region NS may be the liquid-impermeable sheet 41. The rigidity of the front end part 45 of the absorbent body 40 becomes lower than that of the configuration in which the liquid-impermeable sheet 41 and the body sheet 42 are bonded, and the front end part 45 of the absorbent body 40 is easy to deform. In particular, the liquid-impermeable sheet 41 is constituted of a film or the like, and is often higher in rigidity than a liquid-permeable sheet. The sheet non-bonding region NS can reduce the rigidity due to the liquid-impermeable sheet 41, and the front end part 45 of the absorbent body 40 becomes easy to deform.

In addition, the second sheet material is arranged on the skin surface side T1 of the first sheet material, and the first sheet material and the second sheet material may be arranged to straddle a region overlapping the absorbent core 50 and the front end part 45 in the thickness direction T and may be arranged to sandwich the absorbent core 50 in the thickness direction T. The sheet material arranged to sandwich the absorbent core 50 in the thickness direction T is easier to receive the force from the absorbent core 50. Since the sheet non-bonding region NS is provided between the sheet materials arranged to sandwich the absorbent core 50, it is possible to make it further difficult for the force directed from the absorbent body 40 toward the front side to be transmitted to the front exterior body 20, and it is possible to suppress the position shift of the front exterior body 20.

The front end part 45 of the absorbent body 40 may have the first sheet material, the second sheet material located on the skin surface side T1 of the first sheet material, and the third sheet material located on the non-skin surface side T2 of the first sheet material. The liquid-impermeable sheet 41 of one or more embodiments may constitute the first sheet material, the first body sheet 42A may constitute the second sheet material, and the second body sheet 42B may constitute the third sheet material. In such a form, in the sheet non-bonding region NS, the liquid-impermeable sheet 41 may not be bonded to the first body sheet 42A and may not be bonded to the second body sheet 42B. Since the liquid-impermeable sheet 41 is not bonded to the first body sheet and the second body sheet, the liquid-impermeable sheet 41 is easier to deform. Hence, the front end part 45 of the absorbent body 40 becomes easier to deform, thereby suppressing the deformation that the exterior body 15 floats, and allowing the position shift of the exterior body 15 in the front waistline region to be suppressed.

The length in the front-rear direction L of the region where the first sheet material is not bonded to the second sheet material may be longer than the length in the front-rear direction L of the region where the first sheet material is not bonded to the third sheet material. The first sheet material and the second sheet material arranged to sandwich the absorbent core 50 in the thickness direction T are easy to be subjected to the force from the absorbent core 50. Since the length in the front-rear direction L of the region where the first sheet material is not bonded to the second sheet material is relatively long, it is possible to make it further difficult for the force directed from the absorbent body 40 toward the front side to be transmitted to the front exterior body 20, and it is possible to suppress the position shift of the front exterior body 20.

In addition, the cover sheet 27 may be arranged in a position overlapping at least a part of the sheet non-bonding region NS in the thickness direction T. The front end part 45 of the absorbent body 40 is provided with the sheet non-bonding region NS in which the sheet materials are not bonded together, and there is a risk that the front end edge of the sheet material touches the skin. By covering the sheet non-bonding region NS with the cover sheet 27, the front end edge of the sheet material hardly touches the skin, and irritation to the skin can be suppressed.

The cover sheet 27 may be arranged to overlap the entire region of the sheet non-bonding region NS. The entire region of the sheet non-bonding region NS is a region including the entire region of the sheet non-bonding region NS in the front-rear direction and the entire region of the sheet non-bonding region NS in the width direction. By covering the entire region of the sheet non-bonding region NS with the cover sheet 27, it is possible to cover not only the front end edge of the sheet material but also the entire region where the sheet material is easy to float in the thickness direction. Hence, irritation to the skin can be further suppressed.

The absorbent article 10X may have a cover non-bonding region NC where the absorbent body 40 and the cover sheet 27 are not bonded, and a cover bonding region AC where the absorbent body 40 and the cover sheet 27 are bonded. The cover non-bonding region NC may be a region where, among the sheets constituting the absorbent body 40, a sheet arranged to face the cover sheet 27 and the cover sheet 27 are not bonded. The cover bonding region AC may be a region where, among the sheets constituting the absorbent body 40, a sheet arranged to face the cover sheet 27 and the cover sheet 27 are bonded. The cover non-bonding region NC is a region that is lower in rigidity than the region where the cover sheet and the absorbent body 40 are bonded, and that is easy to deform.

The cover non-bonding region NC may be arranged to overlap a part of the sheet non-bonding region NS in the thickness direction. The front end part 45 of the absorbent body 40 is not bonded to the cover sheet and is easy to move with respect to the cover sheet. Even when the cover sheet located on the skin surface side of the wearer adheres closely to the skin, and the cover sheet may hardly deform, the front end part 45 of the absorbent body 40 is easy to deform, thereby suppressing the deformation that the exterior body 15 floats, and allowing the position shift of the exterior body 15 in the front waistline region and the rear waistline region to be suppressed.

In addition, the cover bonding region AC may be arranged to overlap a part of the sheet non-bonding region NS in the thickness direction. A region where the sheet non-bonding region NS and the cover bonding region AC overlap and a region where the sheet non-bonding region NS and the cover bonding region AC do not overlap may be provided. The region where the sheet non-bonding region NS and the cover bonding region AC overlap and the region where the sheet non-bonding region NS and the cover bonding region AC do not overlap are different in rigidity. Gradual deformation occurs when the two regions receive the force from the absorbent core 50, and it is easier to absorb the force received from the absorbent core 50. Hence, it is possible to make it further difficult for the force directed from the absorbent body 40 toward the front side to be transmitted to the front exterior body 20, and it is possible to suppress the position shift of the front exterior body 20.

The cover bonding region AC may be arranged to overlap the sheet bonding region AS in the thickness direction T. The region where the cover bonding region AC and the sheet bonding region AS overlap is higher in rigidity than the region where the cover bonding region AC and the sheet non-bonding region NS overlap or the region where the cover non-bonding region NC and the sheet non-bonding region NS overlap. Since the high rigidity region is provided on the crotch region side relative to the sheet non-bonding region NS, the force directed outward from the absorbent core 50 in the front-rear direction can be dispersed to the sheet material and the cover sheet 27 via the high rigidity region. It is easier to absorb the force received from the absorbent core 50 by both the sheet material and the cover sheet 27. Hence, it is possible to make it further difficult for the force directed from the absorbent body 40 toward the front side to be transmitted to the front exterior body 20, and it is possible to suppress the position shift of the front exterior body 20.

The positional relationship in the width direction W between the sheet non-bonding region NS and the body non-bonding region NB is not limited. The outer end edge of the sheet non-bonding region NS may be outside relative to the outside edge of the body non-bonding region NB, or may be inside relative to the outside edge of the body non-bonding region NB. In one or more embodiments, the sheet non-bonding region NS may extend outside in the width direction W relative to the body non-bonding region NB. Since the sheet non-bonding region NS extends outside in the width direction relative to the body non-bonding region NB, it is possible to reduce rigidity over the entire region in the width direction of the body non-bonding region NB. The deformation of the front end part of the absorbent body makes it easier to suppress deformation such that the exterior body floats.

(4) Absorbent Article According to One or More Embodiments

The absorbent article according to one or more embodiments will be described below with reference to the drawings. It is to be noted that in the following explanation of one or more embodiments, the same components as those of the above embodiments are denoted by the same reference numerals and explanation thereof is omitted.

Figure 8A:
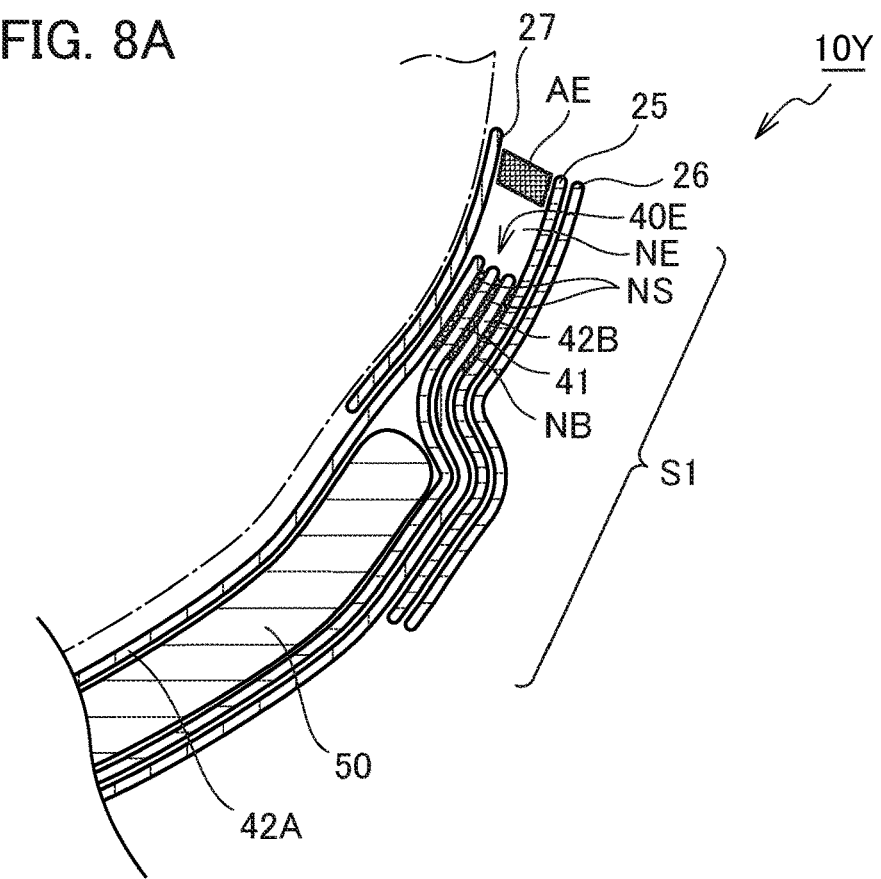
FIGS. 8A and 8B are views each schematically showing a cross section of an absorbent article in a mounted state according to one or more embodiments.
Figure 8B:
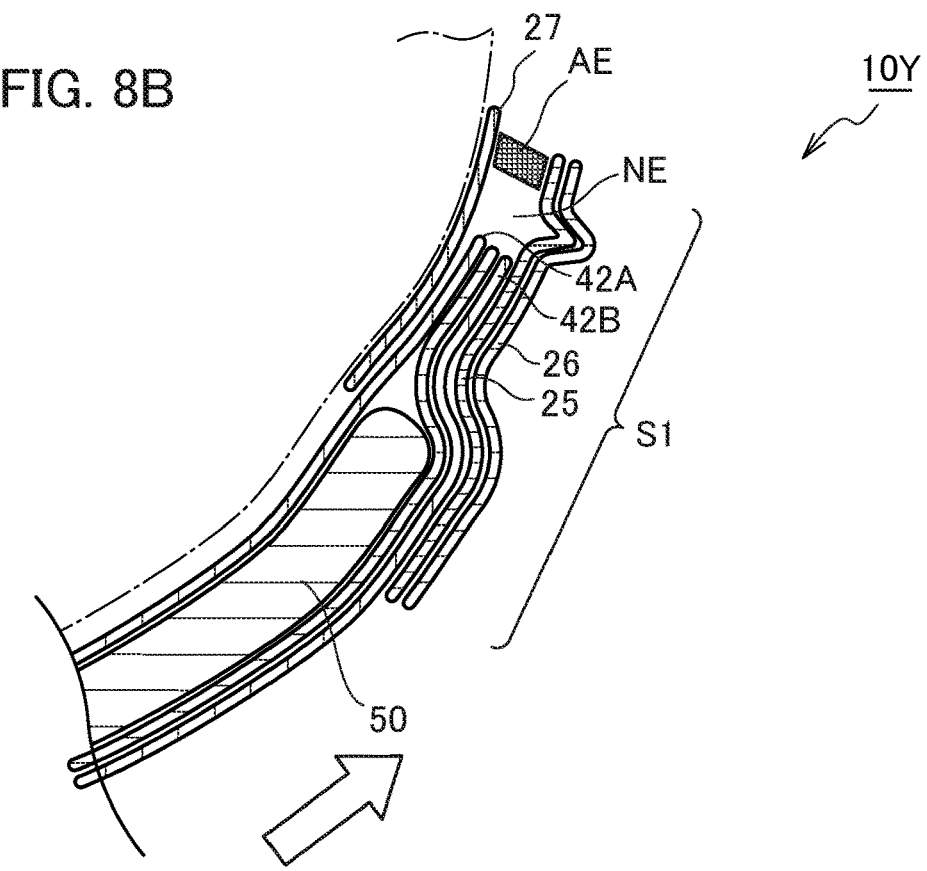
Figure 9A:
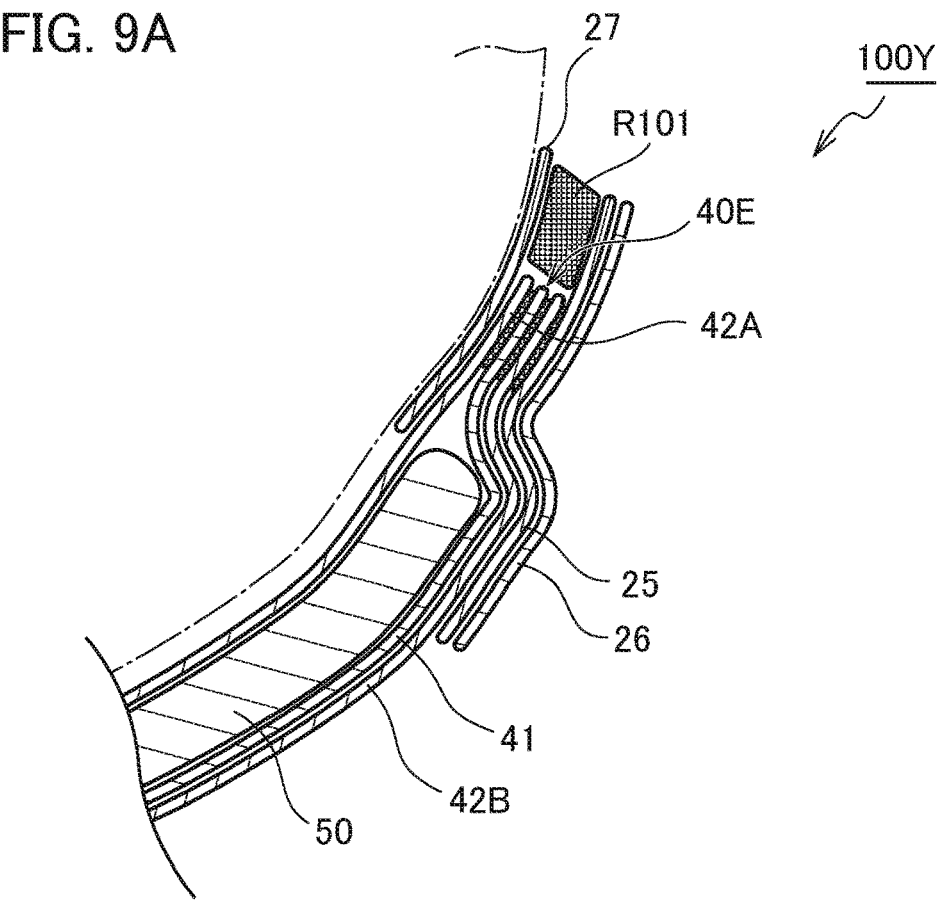
FIGS. 9A and 9B are views each schematically showing a cross section of the absorbent article in a mounted state according to the comparative example of one or more embodiments.
Figure 9B:
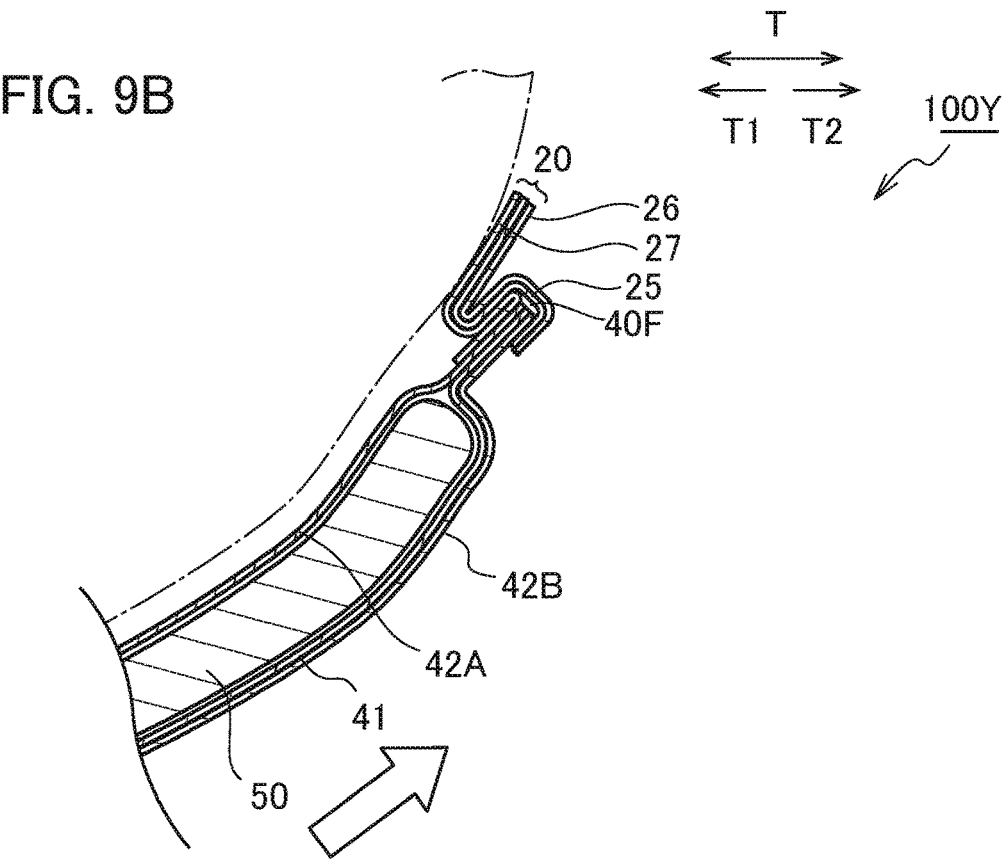

In an absorbent article 10Y according to one or more embodiments, the plane and the cross section shown in FIGS. 1 to 4 are same as those of the above embodiments. FIGS. 8A and 8B are views each schematically showing a cross section of the absorbent article 10Y according to one or more embodiments in a mounted state, and FIGS. 9A and 9B each show a mounted state of an absorbent article 100Y according to the comparative example. FIGS. 8A, 8B, 9A, and 9B schematically show the abdomen of the wearer and the front waistline region of the absorbent article. FIGS. 8A and 9A show a state before deformation, and FIGS. 8B and 9B show a deformed state in which the leg is moved back and forth.

In one or more embodiments, the front exterior body 20 is an exterior body arranged in the front waistline region S1 on the non-skin surface side T2 of the absorbent body 40 and the skin surface side T1 of the absorbent body 40. The front exterior body 20 and the rear exterior body 30 may be constituted of a sheet such as a nonwoven fabric. The front exterior body 20 may have a plurality of exterior sheets. The plurality of exterior sheets may have the exterior non-skin-side sheet located on the non-skin surface side T2 of the absorbent body 40, and the cover sheet 27 located on the skin surface side T1 of the absorbent body 40. The exterior non-skin-side sheet may have a first exterior non-skin-side sheet 25 and a second exterior non-skin-side sheet 26 located on the non-skin surface side T2 of the first exterior non-skin-side sheet 25. The cover sheet 27 may be constituted by a part in which at least one of the plurality of exterior non-skin-side sheets is folded back to the skin surface side T1, or may be constituted by a sheet separate from the exterior non-skin-side sheet. The rear exterior body 30 may have a plurality of exterior sheets.

The absorbent article 10Y according to one or more embodiments may have the exterior non-bonding region NE (See FIGS. 3 and 4) where at least two exterior sheets are not bonded together. The exterior non-bonding region NE is a region where two of the exterior sheets of the first exterior non-skin-side sheet 25, the second exterior non-skin-side sheet 26, and the cover sheet 27 that constitute the exterior sheet are not bonded together. The exterior non-bonding region NE may be provided on the front side relative to the front end edge 40F of the absorbent body 40.

As shown in FIGS. 9A and 9B, the exterior non-bonding region NE is not provided on the front side relative to the absorbent body 40 of the absorbent article 100Y according to the comparative example. The absorbent article 100Y according to the comparative example has the bonding region R101 in which the exterior sheets are bonded together on the front side relative to the front end edge of the absorbent body 40. When the wearer of the absorbent article 100Y thus configured moves his leg back and forth, the absorbent body 40 also moves in the front-rear direction, and the front end edge 40F of the absorbent body 40 moves forward. At this time, the front end edge of the absorbent body may move to the non-skin surface side T2 of the front exterior body 20 so as to roll up the front exterior body 20. In a state where the front end edge 40F of the absorbent body 40 has moved to the non-skin surface side T2 of the front exterior body 20, the front exterior body 20 is sandwiched between the absorbent body 40 and the wearer. In this state, when the front end edge of the absorbent body moves rearward so as to return to the original position, the exterior body is easy to move toward the crotch region side together with the absorbent body. Due to this, the position of the exterior body shifts in the front waistline region, and it may not be possible to continuously cover the abdomen of the wearer.

As shown in FIGS. 8A and 8B, the exterior non-bonding region NE is provided on the front side relative to the absorbent body 40 of the absorbent article 10Y according to one or more embodiments. In the absorbent article 10Y according to one or more embodiments, since the exterior non-bonding region is provided on the front side relative to the front end edge of the absorbent body, the rigidity of the front side relative to the front end edge of the absorbent body becomes low as compared with the configuration in which all the exterior sheets are bonded together. When the front end edge of the absorbent body moves outward in the front-rear direction, the exterior non-bonding region deforms to absorb the force, and it is possible to suppress the front end edge of the absorbent body from moving to the non-skin surface side of the exterior body so as to roll up the exterior body. Hence, it becomes difficult for the exterior body to move toward the crotch region side together with the absorbent body. It is possible to suppress position shift of the exterior body in the front waistline region, and to continuously cover the abdomen of the wearer.

The exterior non-bonding region NE may be provided in a part of the front exterior body 20 or may be provided in the entire region of the front exterior body 20. The front end edge of the exterior non-bonding region NE may coincide with the front end edge 20F of the front exterior body 20, or may be located on the rear side relative to the front end edge 40F of the absorbent body 40. The rear end edge of the exterior non-bonding region NE may be located on the front side relative to the front end edge 40F of the absorbent body 40, may be located on the rear side relative to the front end edge 40F of the absorbent body 40, or may coincide with the front end edge 40F of the absorbent body 40. The outside edge of the exterior non-bonding region NE may coincide with the outside edge 40E of the absorbent body 40, or may be located outside in the width direction W relative to the outside edge 40E of the absorbent body 40.

In one or more embodiments, at least a part of the exterior non-bonding region NE may be arranged to overlap the absorbent core 50 in the front-rear direction L. The region arranged to overlap the absorbent core 50 in the front-rear direction L is easy to be subjected to a force directed from the absorbent core 50 to the front side. By providing the exterior non-bonding region NE in at least a part of the region, when the front end edge 40F of the absorbent body 40 moves forward, the exterior non-bonding region NE deforms to absorb the force, and it is possible to further suppress position shift of the front exterior body 20.

In one or more embodiments, the exterior non-bonding region NE may be arranged to overlap the central region CR in the front-rear direction L. When the wearer moves his leg in the front-rear direction with the absorbent core 50 sandwiched between the legs of the wearer, the force is easy to concentrate on the center of the absorbent core 50 in the width direction W, and the shape of the front end part 45 of the absorbent core 50 is such that the center in the width direction W is easy to project toward the front side relative to the side part in the width direction W. Hence, the region arranged to overlap the central region CR in the front-rear direction L is easier to be subjected to the force directed from the absorbent core 50 to the front side. By providing the exterior non-bonding region NE in the region, when the front end edge 40F of the absorbent body 40 moves forward, the exterior non-bonding region NE deforms to absorb the force, and it is possible to further suppress position shift of the exterior body in the front waistline region S1.

In one or more embodiments, the exterior non-bonding region NE may be arranged to overlap, in the front-rear direction, the entire region in the width direction W of the absorbent core 50. By providing the exterior non-bonding region NE in the region arranged to overlap, in the front-rear direction, the absorbent core 50 in the width direction W, when the front end edge 40F of the absorbent body 40 moves forward, the exterior non-bonding region NE deforms to absorb the force, and it is possible to suppress position shift of the exterior body in the front waistline region S1.

The exterior non-bonding region NE may be provided between the cover sheet 27 and the exterior non-skin-side sheet. The exterior non-skin-side sheet and the cover sheet are arranged to sandwich the absorbent body in the thickness direction, and are easier to receive the force from the absorbent body. By providing the exterior non-bonding region between the exterior non-skin-side sheet and the cover sheet, when the front end edge of the absorbent body moves forward, the exterior non-bonding region deforms to more easily absorb the force, and it is possible to further suppress position shift of the exterior body.

The exterior non-bonding region NE may be provided between the exterior non-skin-side sheets, i.e., between the first exterior non-skin-side sheet 25 and the second exterior non-skin-side sheet 26. Since the exterior non-bonding region is provided between the exterior non-skin-side sheets, when the front end edge of the absorbent body moves outward in the front-rear direction, the front exterior body deforms so as to be tucked to the non-skin surface side, thereby allowing the force to be absorbed. The force from the absorbent body is absorbed by the front exterior body, thereby allowing the position shift of the front exterior body to be suppressed.

The front side relative to the exterior non-bonding region NE may be provided with an exterior bonding region AE where the exterior sheets are bonded together. The exterior sheet bonding region may include a region where the cover sheet 27 is bonded to the exterior non-skin-side sheet and a region where the exterior non-skin-side sheets are bonded together. The exterior bonding region has the exterior sheets bonded together, and is easy to be higher in rigidity than the exterior non-bonding region. In addition, the region in which the absorbent body 40 is arranged is also easy to be higher in rigidity than the exterior non-bonding region. The exterior non-bonding region is sandwiched in the front-rear direction by a high rigidity region, and further deforms when the front end edge 40F of the absorbent body 40 moves toward the front side, thereby becoming easy to absorb the force. It is hence possible to further suppress position shift of the front exterior body 20.

The length of the exterior bonding region AE in the front-rear direction L may be longer than the length of the exterior non-bonding region NE in the front-rear direction L. The exterior bonding region AE is higher in rigidity than the exterior non-bonding region NE, and the length in the front-rear direction L is less easy to become short. By providing a relatively long length of the exterior bonding region AE in the front-rear direction L, it is easy to secure a region covering the waistline by the front exterior body 20.

The cover non-bonding region NC may be provided at the front end part 45 of the absorbent body 40. The cover non-bonding region NC is lower in rigidity than the region where the absorbent body 40 and the exterior body 15 are bonded. By providing the cover non-bonding region NC, it becomes difficult for the force to be transmitted from the absorbent body 40 to the exterior body 15, and it is possible to reduce the force transmitted to the region on the front side relative to the front end edge 40F of the absorbent body 40. It is hence possible to further suppress position shift of the front exterior body 20.

The cover non-bonding region NC may be continuous with the exterior non-bonding region NE in the front-rear direction L. The cover non-bonding region NC and the exterior non-bonding region NE may also shift in the thickness direction, and are only required to be continuous in the front-rear direction. By the cover non-bonding region and the exterior non-bonding region being continuous in the front-rear direction, the region deforming by the force from the absorbent body can be secured long near the front end edge of the absorbent body. It becomes easier for the front exterior body to absorb the force from the absorbent body, and it is possible to further suppress the position shift of the front exterior body.

The length of the exterior non-bonding region NE in the front-rear direction may be longer than the length of the cover non-bonding region NC in the front-rear direction. As compared with a configuration in which the length of the cover non-bonding region in the front-rear direction is longer than that of the exterior non-bonding region, a region deforming by the force from the absorbent body can be secured in the front exterior body, and it is possible to further suppress position shift of the front exterior body.

In addition, in one or more embodiments, the length of the cover non-bonding region in the front-rear direction may be longer than the length of the exterior non-bonding region in the front-rear direction. As compared with a configuration in which the length of the exterior non-bonding region in the front-rear direction is longer than that of the cover non-bonding region, a region deforming by the force from the absorbent body can be secured in the cover sheet, and it is possible to further suppress position shift of the front exterior body.

The absorbent article 10Y may have the body non-bonding region NB where the absorbent body 40 and the exterior non-skin-side sheet are not bonded. The body non-bonding region NB may be a region where, among the sheets constituting the absorbent body 40, the sheet arranged to face the exterior non-skin-side sheet and the exterior non-skin-side sheet are not bonded. Specifically, in the form where the second body sheet 42B is arranged on the entire surface of the non-skin surface of the absorbent body 40, the body non-bonding region NB may be a region where the second body sheet 42B and the exterior non-skin-side sheet are not bonded. In the form where the second body sheet 42B and the liquid-impermeable sheet 41 are arranged on the non-skin surface of the absorbent body 40, the body non-bonding region NB may include a region in which the second body sheet 42B and the exterior non-skin-side sheet are not bonded, and a region in which the liquid-impermeable sheet 41 and the exterior non-skin-side sheet are not bonded. At least a part of the body non-bonding region NB may be provided at the front end part 45. The body non-bonding region NB may be provided in the entire region of the front end part 45 or may be provided in a part of the front end part 45.

The body non-bonding region NB is lower in rigidity than the region where the absorbent body and the exterior non-skin-side sheet are bonded. By providing the body non-bonding region, it becomes difficult for the force to be transmitted from the absorbent body to the exterior body, and it is possible to reduce the force transmitted to the region on the front side relative to the front end edge of the absorbent body. In addition, since the non-skin surface side of the absorbent body is provided with the body non-bonding region, the front exterior body is easy to deform so as to be tucked to the non-skin surface side. It is possible for the front exterior body to further absorb the force from the absorbent body, and it is possible to suppress the position shift of the front exterior body.

The body non-bonding region NB may be continuous with the exterior non-bonding region NE in the front-rear direction. The cover non-bonding region NC and the exterior non-bonding region NE may shift in the thickness direction, and are only required to be continuous in the front-rear direction. By the body non-bonding region NB and the exterior non-bonding region NE being continuous in the front-rear direction, a region deforming by the force from the absorbent body can be secured long near the front end edge of the absorbent body. It becomes easier for the front exterior body to absorb the force from the absorbent body, and it is possible to further suppress the position shift of the front exterior body.

The length of the exterior non-bonding region NE in the front-rear direction L may be longer than the length of the body non-bonding region NB in the front-rear direction L. As compared with a configuration in which the length of the body non-bonding region NB in the front-rear direction L is longer than the length of the exterior non-bonding region NE, it is possible to secure, in the front exterior body 20, a region deforming by the force from the absorbent body 40. It is hence possible to further suppress position shift of the front exterior body 20.

In addition, in one or more embodiments, the length of the body non-bonding region NB in the front-rear direction L may be longer than the length of the exterior non-bonding region NE in the front-rear direction L. Since the body non-bonding region NB is provided on the non-skin surface side T2 of the absorbent body 40, the front exterior body 20 is easy to deform so as to be tucked to the non-skin surface side T2. It is possible for the front exterior body 20 to further absorb the force from the absorbent body 40, and it is possible to suppress the position shift of the front exterior body 20.

The length of the body non-bonding region NB in the front-rear direction L may be longer than the length of the cover non-bonding region NC in the front-rear direction L. The body non-bonding region NB is arranged on the non-skin surface side T2 of the absorbent body 40, and the cover non-bonding region NC is arranged on the skin surface side T1 of the absorbent body 40. Since the length of the body non-bonding region NB in the front-rear direction L is relatively long, the front exterior body 20 is easy to deform so as to be tucked to the non-skin surface side. It is possible for the front exterior body to further absorb the force from the absorbent body, and it is possible to suppress the position shift of the front exterior body.

In addition, since the front end part 45 of the absorbent body 40 is provided with the duplicating region DR, the duplicating region DR is easier to deform when a force moving forward is applied from the absorbent core 50. The deformation of the front end part 45 of the absorbent body 40 can reduce the force transmitted to the region on the front side relative to the front end edge 40F of the absorbent body 40, suppress position shift of the front exterior body 20, and continuously cover the abdomen of the wearer.

The front end edge of the sheet non-bonding region NS and the front end edge of the body non-bonding region NB may coincide with the front end edge 40F of the absorbent body 40, or may be located on the rear side relative to the front end edge 40F of the absorbent body 40. The rear end edge of the sheet non-bonding region NS and the rear end edge of the body non-bonding region NB may be located on the front side relative to the front end edge 50F of the absorbent core 50, may be located on the rear side relative to the front end edge 50F of the absorbent core 50, or may coincide with the front end edge 50F of the absorbent core 50. The outside edge of the sheet non-bonding region NS and the outside edge of the body non-bonding region NB may coincide with the outside edge 40E of the absorbent body 40, or may be located inside the width direction W relative to the outside edge 40E of the absorbent body 40. In one or more embodiments, the body non-bonding region NB and the sheet non-bonding region NS may be provided at the front end edge of the absorbent body 40. The front end edge of the absorbent body 40 is provided with both the body non-bonding region NB and a sheet non-bonding region NS, and hence the absorbent body is easier to deform. The deformation due to the absorbent core 50 is absorbed by the front end edge of the absorbent body 40, and it is possible to reduce the force transmitted to the region on the front side relative to the front end edge 40F of the absorbent body 40, to suppress position shift of the front exterior body 20, and to continuously cover the abdomen of the wearer.

The sheet non-bonding region NS may be any of a region where the liquid-impermeable sheet 41 is not bonded to the first body sheet 42A, a region where the liquid-impermeable sheet 41 is not bonded to the second body sheet 42B, and a region where the liquid-impermeable sheet 41 is not bonded to the first body sheet 42A and the second body sheet 42B. In one or more embodiments, in the sheet non-bonding region NS, the liquid-impermeable sheet 41 may not be bonded to the first body sheet 42A and may not be bonded to the second body sheet 42B. Since the liquid-impermeable sheet 41 is not bonded to the first body sheet and the second body sheet, the liquid-impermeable sheet 41 is easier to deform. Hence, the front end part 45 of the absorbent body 40 becomes easier to deform, and it is possible to reduce the force transmitted to the region on the front side relative to the front end edge 40F of the absorbent body 40, to suppress position shift of the front exterior body 20, and to continuously cover the abdomen of the wearer.

While one or more embodiments of the present invention have been described in detail, it is obvious to those skilled in the art that the present invention is not limited to the embodiments described herein. One or more embodiments of the present invention can be implemented as modifications and variations without departing from the spirit and scope of the present invention defined by the descriptions of the claims. Accordingly, the descriptions herein are intended to be illustrative and has no restrictive meaning to the present invention.

INDUSTRIAL APPLICABILITY

It is possible to provide an absorbent article which can suppress the position shift of the exterior body in the front waistline region by moving the leg of the wearer.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE NUMERALS 10, 10X, 10Y Absorbent article
15 Exterior body
20 Front exterior body
25 First exterior non-skin-side sheet (exterior sheet)
26 Second exterior non-skin-side sheet (exterior sheet)
27 Cover sheet (exterior sheet)
30 Rear exterior body
40 Absorbent body
41 Liquid-impermeable sheet
42A First body sheet (body sheet)
42B Second body sheet (body sheet)
45 Front end part
50 Absorbent core
60 Side bonded portion
AC Cover bonding region
AE Exterior bonding region
AS Sheet bonding region
DR Duplicating region
OR Overlapping region
NB Body non-bonding region
NC Cover non-bonding region
NE Exterior non-bonding region
NS Sheet non-bonding region
S1 Front waistline region
S2 Rear waistline region
S3 Crotch region
L Front-rear direction
W Width direction

What is claimed is:

1. An absorbent article having a front-rear direction and a width direction orthogonal to the front-rear direction, comprising:
   a front waistline region;
   a rear waistline region;
   a crotch region disposed between the front waistline region and the rear waistline region;

an absorbent body that straddles the crotch region, the front waistline region, and the rear waistline region; and a front exterior body disposed in the front waistline region on a non-skin surface side of the absorbent body, wherein the absorbent body comprises an absorbent core and a front end part extending toward a front side of the absorbent article from the absorbent core, a liquid-impermeable sheet and a liquid-permeable body sheet overlapping the liquid-impermeable sheet in a thickness direction are disposed in the front end part, the absorbent article further comprises:
    a sheet non-bonding region where the liquid-impermeable sheet and the body sheet are not bonded; and
    a body non-bonding region where the absorbent body and the front exterior body are not bonded, the front end part comprises a duplicating region where the sheet non-bonding region and the body non-bonding region overlap each other, the liquid-impermeable sheet and the body sheet straddle the front end part and a region overlapping the absorbent core in the thickness direction, the liquid-impermeable sheet and the body sheet sandwich the absorbent core in the thickness direction, a sheet bonding region is disposed closer to the crotch region than the sheet non-bonding region, the liquid-impermeable sheet and the body sheet are bonded to each other in the sheet bonding region, and an inner end edge of the sheet non-bonding region on a crotch region side is disposed closer to the front side of the absorbent article than the absorbent core.

2. The absorbent article according to claim 1, wherein at least a part of the duplicating region overlaps the absorbent core in the front-rear direction.

3. The absorbent article according to claim 2, wherein
the absorbent body comprises a central region at a center of the absorbent core in the width direction,
the central region is obtained by dividing a total length of the absorbent core in the width direction into three equal parts, and
the duplicating region overlaps the central region in the front-rear direction.

4. The absorbent article according to claim 2, wherein the duplicating region overlaps, in the front-rear direction, an entire region of the absorbent core in the width direction.

5. The absorbent article according to claim 1, wherein the body non-bonding region is disposed at a front end edge of the absorbent body.

6. The absorbent article according to claim 1, wherein the sheet non-bonding region extends toward the crotch region farther than the body non-bonding region.

7. The absorbent article according to claim 1, further comprising:
a cover sheet disposed on a skin surface side of the absorbent body, wherein
the sheet non-bonding region overlaps, in the thickness direction, at least a part of a cover non-bonding region where the absorbent body and the cover sheet are not bonded to each other.

8. An absorbent article having a front-rear direction and a width direction orthogonal to the front-rear direction, comprising:
a front waistline region;
a rear waistline region;
a crotch region disposed between the front waistline region and the rear waistline region;
an absorbent body that straddles the crotch region, the front waistline region, and the rear waistline region; and a front exterior body disposed in the front waistline region on a non-skin surface side of the absorbent body, wherein the absorbent body comprises an absorbent core and a front end part extending toward a front side of the absorbent article from the absorbent core, a liquid-impermeable sheet and a liquid-permeable body sheet overlapping the liquid-impermeable sheet in a thickness direction are disposed in the front end part, the absorbent article further comprises:
    a sheet non-bonding region where the liquid-impermeable sheet and the body sheet are not bonded; and
    a body non-bonding region where the absorbent body and the front exterior body are not bonded, the front end part comprises a duplicating region where the sheet non-bonding region and the body non-bonding region overlap each other, the sheet non-bonding region extends outward in the width direction further than the body non-bonding region, the liquid-impermeable sheet and the body sheet straddle the front end part and a region overlapping the absorbent core in the thickness direction, the liquid-impermeable sheet and the body sheet sandwich the absorbent core in the thickness direction, a sheet bonding region is disposed closer to the crotch region than the sheet non-bonding region, the liquid-impermeable sheet and the body sheet are bonded to each other in the sheet bonding region, and an inner end edge of the sheet non-bonding region on a crotch region side is disposed closer to the front side of the absorbent article than the absorbent core.

9. An absorbent article having a front-rear direction and a width direction orthogonal to the front-rear direction, comprising:
a front waistline region;
a rear waistline region;
a crotch region disposed between the front waistline region and the rear waistline region;
an absorbent body that straddles the crotch region, the front waistline region, and the rear waistline region; and a front exterior body disposed in the front waistline region on a non-skin surface side of the absorbent body, wherein the absorbent body comprises an absorbent core and a front end part extending toward a front side of the absorbent article from the absorbent core, a liquid-impermeable sheet and a liquid-permeable body sheet overlapping the liquid-impermeable sheet in a thickness direction are disposed in the front end part, the absorbent article further comprises:
    a sheet non-bonding region where the liquid-impermeable sheet and the body sheet are not bonded; and
    a body non-bonding region where the absorbent body and the front exterior body are not bonded, the front end part comprises a duplicating region where the sheet non-bonding region and the body non-bonding region overlap each other, the body sheet comprises:
    a first body sheet disposed closer to a skin surface side of the absorbent body than the liquid-impermeable sheet; and a second body sheet disposed closer to the non-skin surface side than the liquid-impermeable sheet, in the sheet non-bonding region, the liquid-impermeable sheet is not bonded to the first body sheet and is not bonded to the second body sheet, the liquid-impermeable sheet and the body sheet straddle the front end part and a region overlapping the absorbent core in the thickness direction, the liquid-impermeable sheet and the body sheet sandwich the absorbent core in the thickness direction, a sheet bonding region is disposed closer to the crotch region than the sheet non-bonding region, the liquid-impermeable sheet and the body sheet are bonded to each other in the sheet bonding region, and an inner end edge of the sheet non-bonding region on a crotch region side is disposed closer to the front side of the absorbent article than the absorbent core.

10. The absorbent article according to claim 1, wherein a front end edge of the body non-bonding region and a front end edge of the sheet non-bonding region coincide with a front end edge of the absorbent body.

\* \* \* \* \*